US006828144B2

(12) United States Patent
Downs

(10) Patent No.: US 6,828,144 B2
(45) Date of Patent: Dec. 7, 2004

(54) METHOD OF OBSERVING VASCULOGENESIS IN VITRO USING CULTURED ALLANTOIS

(75) Inventor: Karen M. Downs, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

(21) Appl. No.: 09/336,103

(22) Filed: Jun. 18, 1999

(65) Prior Publication Data

US 2002/0039572 A1 Apr. 4, 2002

Related U.S. Application Data

(63) Continuation-in-part of application No. 08/838,384, filed on Apr. 8, 1997, now abandoned.
(60) Provisional application No. 60/015,066, filed on Apr. 9, 1996, and provisional application No. 60/118,764, filed on Feb. 5, 1999.

(51) Int. Cl.[7] .............................................. C12N 15/85
(52) U.S. Cl. ..................................................... 435/325
(58) Field of Search ........................... 435/325; 800/4; 424/93.2, 93.21, 93.7

(56) References Cited

PUBLICATIONS www.dictionary.com, enter "mesenchymal" Dec. 2000 (internet).
Ribatti et al., New Model for the Study of Angiogenesis and Antiangiogenesis in the Chick Embryo Chorioallantoic Membrane: The Gelatin Sponge/Chorioallantoic Membrane Assay, 1997, vol. 34:455–463.
Downs et al., Developmental Potency of the murine allantois, Jul. 1997, Development, vol. 124 pp. 2769–2780.
Coutelle, et al., "The Challenges of Fetal Gene Therapy," Nature Medicine, 1:864–866 (Sep. 1995).
Douar, et al., "Foetal Gene Delivery in Mice by Intra–Amniotic Administration of Retroviral Producer Cells and Adenovirus," Gene Therapy, 4:883–890 (1997).
K.M. Downs and R.L. Gardner, "An investigation into early placental ontogeny: allantoic attachment to the chorion is selective and developmentally regulated," Development, 121:407–416 (1995).
K.M. Downs, et al., "Vascularization in the Murine Allantois occurs by Vasculogenesis without Accompanying Erythropoiesis," Development 125:4507–4520 (1998).
S.K.L. Ellington, "A morphological study of the development of the allantois of rat embryos in vivo," J. Anat. 142:1–11 (1985).
Fletcher, et al., "Human Fetal Gene Therapy: Moral and Ethical Questions," Human Gene Therapy, 7:1605–1614 (Aug. 20, 1996).
Orkin, et al., "Report and Recommendations of the Panel to Assess the NIH Investment in Research on Gene Therapy," National Institute of Health, Bethesda, MD (Dec. 7, 1995).
Verma, et al., "Gene Therapy–Promises, Problems, and Prospects," Nature, 389:239–242 (Sep. 18, 1997).

Primary Examiner—Michael Wilson
(74) Attorney, Agent, or Firm—Quarles & Brady LLP

(57) ABSTRACT

A method of fetal gene therapy is disclosed. In general, the method comprises the steps of identifying a fetus with a genetic defect, obtaining allantois/umbilical cord cells expressing a gene product that ameliorates the genetic defect, and exposing the fetus to the allantois/umbilical cord cells wherein a chimeric allantois is capable of supplying the gene product to the fetus is created. The present invention is also a method of examining the effect of test compounds on vasculogenesis and angiogenesis by observing the effect of the test compound on cultured allantoic explants.

2 Claims, 19 Drawing Sheets

1. Isolate LacZ-expressing allantois cells and infect with retrovirus carrying Factor VIII
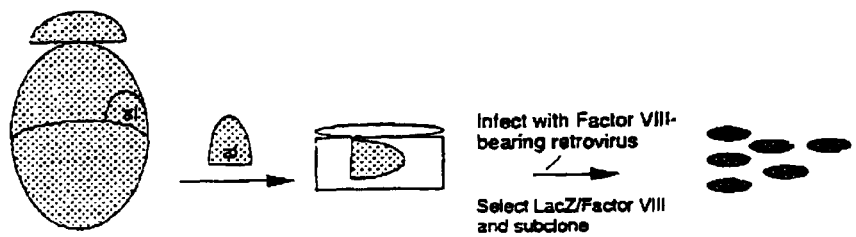
2. Inject LacZ-Factor VIII-expressing allantois cells into Factor VIII-defective embryos
FIG. 2

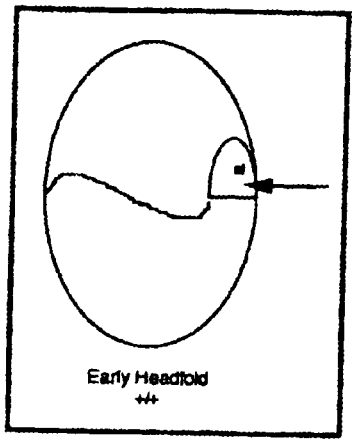

Early Headfold
+/+

| Summary of Grafts into the Base of the Allantois | | | |
|---|---|---|---|
| Region Grafted→<br>Region Colonized ↓ | Base | Mid-Portion | Tip |
| Base | + | + | 0 |
| Mid-Region | ■■■ | ▦▦▦ | ▦▦▦ |
| Distal Third | ▦▦▦ | ▦▦▦ | ■■■ |
| Vitelline Omphalomes Artery | + | + | |
| No. Chimeras with Unincorporated Donor Cells | 1 | 2 | 0 |
| Initial Stage of Host Embryoss | Headfold | Headfold, 3-5 | Headfold, 3 |
| Final Number Somite Pairs | 10-16 | 8-16 | 11-16 |
| Total Number of Incorporated Transgenic Cells | 5652 | 9715 | 2501 |
| Number Chimeras (% Total Injected) | 21 (60.0%) | 16 (76.2%) | 12 (85.7%) |

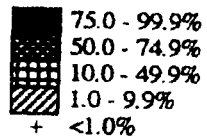
 75.0 - 99.9%
 50.0 - 74.9%
 10.0 - 49.9%
 1.0 - 9.9%
+  <1.0%

FIG. 5

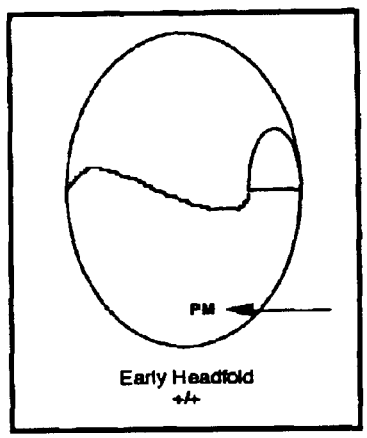

Early Headfold
+/+

| | Orthotopic: Prospective Paraxial Mesoderm | Heterotopic: Allantois to Prospective Paraxial Mesoderm | | |
|---|---|---|---|---|
| Tissue Grafted→<br>Tissue Colonized ↓ | PM | Base | Mid-Portion | Tip |
| Somites | ▓▓ | | | |
| Pre-Somitic Mesoderm | ▓▓ | | | |
| Capillaries (in neurectoderm) | ▓▓ | | | |
| Neural Tube | ▓▓ | | | |
| Notochordal Plate | ▓▓ | | | |
| Surface Ectoderm | + | | | |
| Endothelium of Intersegmental Vessels | | ▓▓ | ▓▓ | |
| Endothelium of Dorsal Aorta | | ▓▓ | ▓▓ | ▓▓ |
| Mesenchyme Adj to Dorsal Aorta | | | ▓▓ | ▓▓ |
| No. Chimeras with Unincorporated Donor Cells | 1 | 0 | 4 | 1 |
| Initial Stage of Host Embryos | Headfold, 3-4 | Headfold | Headfold, 1 | Headfold |
| Final Number Somite Pairs | 10-14 | 9-11 | 8-13 | 11-13 |
| Total Number of Incorporated Transgenic Cells | 1021 | 136 | 1060 | 340 |
| Number Chimeras (% Total Injected) | 7 (33.3%) | 2 (10.5%) | 6 (28.6%) | 4 (30.8%) |

Summary of Transplants into the Primitive Streak at the Level of Prospective Paraxial Mesoderm

METHOD OF OBSERVING VASCULOGENESIS IN VITRO USING CULTURED ALLANTOIS

CROSS-REFERENCE TO RELATED APPLICATION

This application is a continuation-in-part of to U.S. Ser. No. 08/838,384 (abandoned), filed Apr. 8, 1997, U.S. Ser. No. 60/015,066, filed Apr. 9, 1996 and to U.S. Ser. No. 60/118,764, filed Feb. 5, 1999.

STATEMENT REGARDING FEDERALLY SPONSORED RESEARCH OR DEVELOPMENT

This invention was made with United States government support awarded by the following agencies: NIH HD36847. The United States has certain rights in this invention.

BACKGROUND OF THE INVENTION

The major vascular systems of the developing fetus are formed by vasculogenesis, a developmental process in which mesoderm is transformed in situ into endothelial cells. The goal of my work is to discover how mesoderm is transformed into the endothelial cell lineage using the mouse allantois as a model in vitro system.

During its early development, the murine allantois consists of an inner core of mesoderm and an outer layer of squamous epithelium referred to as a mesothelium. The allantois undergoes two major developmental processes:

(i) maturation and fusion with the chorion to become the umbilical component of the chorioallantoic placenta, and (ii) vascularization, forming an artery and a vein that permit within the chorionic disk the exchange of nutrients, metabolic wastes and gases with the mother during fetal gestation (K. M. Downs and R. L. Gardner, *Development* 121:407–416, 1995; K. M. Downs and C. Harmann, *Development* 124:2769–2780, 1997; K. M. Downs, et al., The Murine Allantois. In Current Topics in Developmental Biology (eds. R. Pedersen and G. Schatten). New York: Academic Press. 39:1–33, 1998; K. M. Downs, supra, 1998).

BRIEF SUMMARY OF THE INVENTION

In one embodiment, the present invention is a method for evaluating the effect of test compounds, preferably potentially harmful or beneficial substances, on formation of blood vessels during vasculogenesis. In one embodiment, this method comprises direct application of a test compound to cultured allantoic explants. In another embodiment, one would evaluate test compounds by DNA uptake and expression of a test compound by the mesenchymal cells of allantoic explants.

In another embodiment, the present invention is the delivery of factors into the umbilical circulation by formation of chimeric allantoises. Preferably, this delivery ameliorates or eliminates developmental defects through delivery of therapeutic factors.

In another embodiment, the present invention is the delivery of factors into the umbilical circulation by formation of chimeric allantoises. Preferably, this delivery ameliorates or eliminates developmental defects through delivery of therapeutic factors found in normal allantoic cells.

In another embodiment, the present invention is the delivery of gene expression products into the umbilical circulation by formation of a chimeric allantois. This method comprises the step of transfection of mesenchymal cells with heterologous genes expressed from appropriate endothelial cell promoters and introducing the donor mesenchymal cells into a developing allantois. Once integrated into the vasculature, the cells will express the gene product and deliver it to the bloodstream of the fetus. Preferably, the gene product is a therapeutic protein targeted to a fetus with particular developmental defects.

In another embodiment, the present invention is a method of fetal gene therapy comprising the step of creating a chimeric allantois/umbilical cord. Specifically, the method involves identifying a fetus with a genetic defect and obtaining compatible allantois/umbilical cells capable of expressing a gene product that would ameliorate this defect. The cells are introduced into the exocelomic cavity of the defective embryo or transplanted into the conceptus and assimilated into the native allantois/umbilical cord. Thus, a chimeric allantois/umbilical cord is produced. The gene product is then delivered into the fetus via the umbilical blood vessels. Preferably, the fetus is a mammalian fetus. Most preferably, the fetus is a human fetus.

In another embodiment, the present invention is a method of delivering a heterologous protein to a fetus via obtaining compatible allantois/umbilical cells capable of expressing a gene product and introducing these cells into the exocelomic cavity of an embryo or transplanting the cells onto the embryo and assimilating them into the native allantois/umbilical cord. A chimeric allantois/umbilical cord is produced and the gene product is then delivered into the fetus via the umbilical blood vessels.

In another embodiment, the present invention is a method of fetal gene therapy comprising the step of creating a chimeric allantois/umbilical cord by obtaining allantois cells compatible with a fetus with a genetic defect that express a gene product that ameliorates the genetic defect. The cells are then transplanted into the fetus wherein the transplanted cells develop into endothelial cells which line the vasculature of the umbilical cord and release the gene product into the bloodstream of the fetus.

The present invention is also a population of transgenic allantois cells, wherein the transgene may be a therapeutic gene and/or a marker or reporter gene.

It is an object of the present invention to provide a method of human fetal gene therapy.

It is another object of the present invention to provide a method of human fetal gene therapy that would benefit continued therapy after birth because the supplemented gene product would be recognized as "self" by the adult immune system.

Other advantages, objects and features of the present invention will be obvious after review of the specification, drawings and claims.

BRIEF DESCRIPTION OF SEVERAL VIEWS OF THE DRAWINGS

FIG. 1A depicts the allantois of a ROSA26/26-expressing headfold-stage conceptus.

FIG. 2 is a schematic diagram of fetal gene therapy.

FIG. 5 is a summary of results of grafts of donor allantoic tissue into the base of host allantoises, headfold stage.

FIG. 7 is a summary of results of grafts into prospective paraxial mesoderm, headfold stage.

FIGS. 10A–C describe the comparison of a single explanted allantois grown for 24 hours (FIG. 10A), 48 hours (FIG. 10B) and 72 hours (FIG. 10C) in a 24-well tissue culture plate containing an equal volume of rat serum and DMEM. FIGS. 10D–F show vascular channels, coalesced clusters of cells, and peripheral mesenchymal cells.

FIGS. 11A and B are low and high magnification of anti-Flk-1-stained allantoises. FIGS. 11C and D are low and high magnification of anti-VCAM-1-stained allantoises. FIGS. 11E and F are control allantoises minus primary antibody (FIG. 11E) and primary antibody prebound with control peptide (FIG. 11F).

FIG. 12A is at 4 hours, FIG. 12B is at 8 hours, FIG. 12C is at 12 hours, FIG. 12D is at 16 hours and FIG. 12E is at 20 hours.

FIG. 13A is a 8.75 dpc cultured benzidine-stained host conceptus viewed from the region of the ectoplacental cone to show the vessel-free region in the yolk sac selected for injection of donor cells into the allantois.

FIG. 13B is a schematic diagram of cultured 8.75 dpc conceptus in sagittal orientation showing the distal site of injection of donor cells into the host allantois.

FIG. 13C is an operated 8.75 dpc host conceptus cultured for a further 8 hours, viewed following removal of its yolk sac. FIG. 13D is a schematic diagram of the fetus in (13C) showing the regions of the allantois used to score the location of blue donor cells. FIG. 13E demonstrates cultured lacZ/+ blue donor cells are visible in the distal and fusion junction regions of the host allantois. (The insert is a higher magnification view of donor cells in the chorioallantoic fusion junction showing incorporation of donor cells in the host endothelium.) FIG. 13F is a clump of unincorporated donor cells in contact with, but not integrated into, the host yolk sac.

FIG. 15D is a higher magnification view of doubly-stained X-gal/Flk-1-positive donor cells.

FIG. 17A is an allantois at late headfold-stage (LHF). FIG. 17B is an allantois at 4-somite pairs. FIG. 17C is a 6-somite pair allantois. FIG. 17D is an 8-somite pair allantois. FIG. 17E is an 8-somite pair control conceptus without antibody (−Ab). FIG. 17F is an 8-somite pair control allantois in which antibody to VCAM-1 was prebound with control VCAM-1 peptide (+cp).

FIG. 18A is a freshly recovered conceptus containing 14-somite pairs. FIG. 18B is a headfold-stage conceptus cultured to 14-somite pairs. FIG. 18C is an explanted headfold stage allantois cultured in suspension for 24 hours and doubly-immunostained.

DETAILED DESCRIPTION OF THE INVENTION

Figure 1:
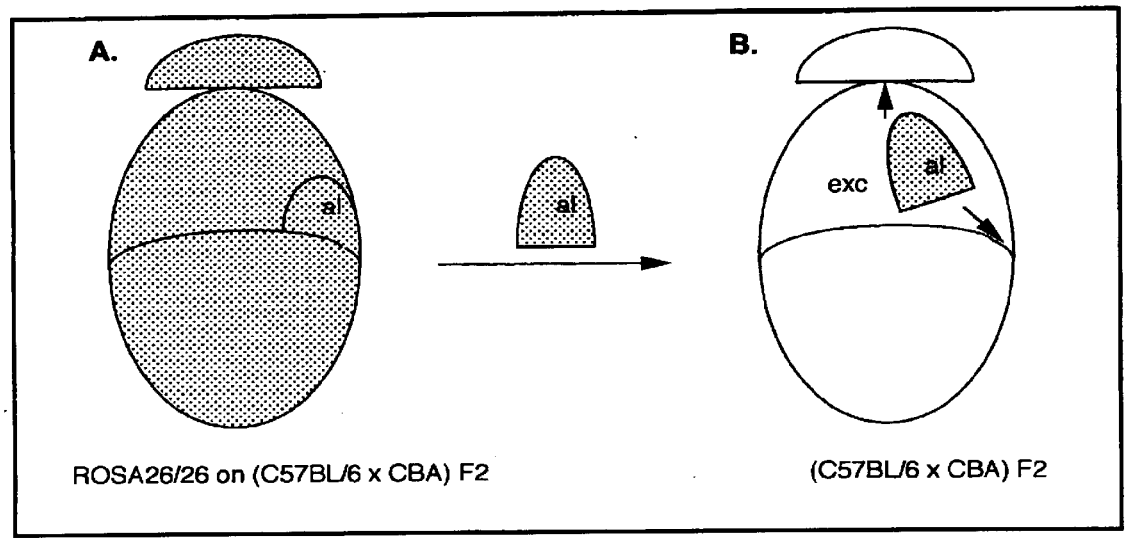
FIGS. 1A and B depict microsurgery of ROSA26/26 allantoises into genetically-similar non-transgenic hosts.
FIG. 1B depicts injecting the allantois into the exocelomic cavity of a congenic non-transgenic host.

1. Method of Delivering Therapeutic Molecules to a Fetus

The present invention is a method of delivering molecules, preferably therapeutic molecules, to a fetus. In one embodiment, this method begins with identifying a fetus with a genetic defect. Once one has identified this defect, one then must obtain compatible allantois cells capable of expressing a gene that would ameliorate this defect. (These cells could be recombinant cells expressing a foreign gene product or non-recombinant cells expressing native gene products.) The Examples below describe a proposed method of ameliorating hemophilia A in transgenic mice defective in production of Factor VIII with genetically-engineered cells which can assimilate into the allantois and/or umbilical cord to form a chimeric umbilical cord. Of course, other genetic defects and diseases are known to one of skill in the art of molecular biology.

We propose below to obtain compatible allantois or umbilical cord cell lines that will then be manipulated to express factor VIII. By "compatible," we mean cells that may be assimilated into the native allantois to make a chimeric allantois or umbilical cord. As described in the Examples, whole allantoises from appropriate conceptuses are removed with glass capillary pipettes and placed in tissue culture dishes. When the explants are fairly large, they will be disaggregated and passaged into cells to reach confluence. These cells will be subcloned, transfected and tested for the appropriate gene activity. Alternatively, one might infect explants rather than cell lines and subclone after infection.

The present invention is also a transgenic allantois cell. The transgene may be a therapeutic gene or a marker gene.

The Examples below demonstrate that cells taken from different areas of the allantois seem to have different developmental potentials.

In the allantois, the transplanted cells appeared as various cell types, including endothelial cells which would be expected to line the vasculature of the umbilical cord. Thus, these transplanted cells could potentially be useful for releasing the products of transfected genes into the bloodstream of a developing fetus. Genetic engineering of these allantoic cells could also be useful for studying the function of various genes in normal vasculogenesis and in malfunctions of vasculogenesis.

It may therefore be advantageous in some applications to obtain cells from only one portion of the allantois and manipulate and transplant these specially selected cells. For example, the examples below describe the appearance of transgenic endothelial cells after transplantation of transgenic allantois cells onto a non-transgenic fetus. Other experiments suggest to us that cells of the mid-region, as described below in the Examples, might be the most effective. Alternatively, the cells of the base of the allantois seem to be more pluripotent and these cells might be selected for other applications.

Additionally, the Examples below suggest that the location of the cell transplant can determine allantoic cell development. Other applications might require that the allantois cells be transplanted specifically to a particular location to achieve redirected allantoic development, according to the new host site. For example, allantoic cells from the appropriate allantoic region may be placed into the liver where the liver redirects allantoic cells to differentiate into the endothelium characteristic of the vasculature of liver cells.

In a particularly advantageous form of the present invention, one obtains allantois cells compatible with the fetus and transplants the allantois cells to the fetus wherein the transplanted cells develop into endothelial cells which line the vasculature of the umbilical cord and release the desired gene product into the bloodstream of the fetus.

It is useful in the Examples below to work with cells containing a marker gene, such as the LacZ gene. The presence of a marker gene enables one to easily monitor whether the foreign cells have integrated with the native allantois.

Once appropriate allantois cells have been produced, the cells will be injected into the exocelomic cavity of the defective embryo or transplanted directly onto a particular region of the fetus. Assimilation of the cells into the native allantois should commence and thus, delivery of factor VIII to the fetus. Preferably, the cells will be transplanted directly into the umbilical cord or into a particular region of the fetus.

For human gene therapy, allantois or fetal umbilical cord cells may be obtained from an aborted or miscarried fetus.

The present invention is also a method of fetal gene therapy comprising identifying a fetus with a genetic defect, and obtaining allantois or umbilical cord cells compatible with the fetus, wherein the cells express a gene product that ameliorates the genetic defect. These cells are also capable of colonizing a fetal organ. One then exposes the fetus to the cells. A chimeric fetal organ capable of supplying the gene product to the fetus is created. By "organ" we mean to include the blood circulatory system. Preferably, the fetal organ is a liver or aorta. Preferably, the method of exposure is microinjection of the cells into the fetal organ.

2. In Vitro System of Vasculogenesis

We have discovered, as demonstrated below in Section II, that the allantois vascularizes by vasculogenesis that is not accompanied by erythropoiesis. Transformation of core allantoic mesoderm into the endothelial cells of blood vessels initially occurs along a spatial gradient, with the cells more distal to the embryo farther along in their developmental program than those more proximal (K. M. Downs and C. Harmann, supra, 1997; K. M. Downs, et al., supra, 1998). How core allantoic mesoderm differentiates is not known, though results of our studies strongly implicate allantoic mesothelium as a key player in this transformation, because mesothelial cell formation coincides with, or possibly precedes vascularization in core mesoderm.

Moreover, Flk-1, an early marker of endothelial cells, is expressed only in core mesoderm, whereas Flk-1's ligand, vascular endothelial growth factor (VEGF), is expressed in the overlying mesothelium, invoking a paracrine system of differentiation between mesothelium and core mesoderm.

Therefore, in one embodiment, the present invention is a method for evaluating the effect of test compounds, preferably potentially harmful or beneficial substances, on formation of blood vessels during vasculogenesis. This method may comprise direct application of a test compound to cultured allantoic explants, as described in Section II and U.S. Ser. No. 08/838,384. In another embodiment, one would evaluate test compounds by DNA uptake and expression of a test compound by the mesenchymal cells of allantoic explants.

Inhibitors of vasculogenesis are known to affect angiogenesis (see M. S. Pepper, et al., *Cytokine and Growth Factor Reviews* 8:21–43, 1997). Pepper, et al. show that transforming Growth Factor beta (TGFbeta) has different functions on vessel formation at different stages in the process and regulates formation of blood vessels (vasculogenesis) by potentiating or inhibiting the activity of positive regulators such as basic Fibroblast Growth Factor (bFGF) and Vascular Endothelial Growth Factor (VEGF) in a concentration-dependent manner. On the other hand, once a vessel has formed, TGFbeta1 promotes maintenance of endothelial cell quiescence and induces vessel maturation (both vasculogenesis and angiogenesis). Therefore, we expect that the test compounds found to modulate vasculogenesis will modulate angiogenesis as well.

Relevance of the Mouse Conceptus as a Model System for Development of the Chorioallantoic Placenta Many eutherian mammals, including humans and rodents, survive and develop within the uterine environment through the formation of a chorio-allantoic placenta. Although fine details may vary, all placentae contain an umbilical circulation that consists of at least one major artery and vein. Without exception, these major blood vessels transport fetal blood to and from the chorionic disc for the exchange of nutrients, metabolic wastes and gases with the mother (H. W. Mossman, *Vertebrate Fetal Membranes*. MacMillan Press Ltd: Basingstoke, UK, 1987).

The mouse is an ideal model system for the study of umbilical development for several reasons. First, formation of the placenta occurs on schedule in whole embryo culture of living mouse conceptuses (K. M. Downs and R. L. Gardner, supra, 1995; K. M. Downs, et al., supra, 1998). Second, the allantois, precursor of the umbilical cord, is particularly amenable to manipulation in vitro and can be isolated free of contamination from the conceptus (K. M. Downs and R. L. Gardner, supra, 1995; K. M. Downs and C. Harmann, supra, 1997; K. M. Downs, et al., supra, 1998; reviewed in K. M. Downs, supra, 1998) Third, transgenic mouse technology has enabled the identification of genes involved in formation of the placenta, either because its two major components, the allantois and the chorion, do not unite in the mutant mice (G. C. Gurtner, et al., *Genes and Dev.* 9:1–14, 1995; L. Kwee, et al., *Development* 121:489–503, 1995; J. T. Yang, et al., *Development* 121:549–560, 1995) or because vasculogenesis has not occurred in the umbilicus (R. J. Akhurst, et al., *Development* 108:645–656, 1990; M. C. Dickson, et al., *Development* 121:1845–1854, 1995; F. Shalaby, et al., *Nature* 376:62–66, 1995). Thus, the mouse is an ideal system in which to elucidate the genetic control of major developmental processes. There exists no other mammalian model at this time that exhibits all of these significant strengths.

Description of the Technique of in vitro Vasculogenesis, Applications, and Preliminary Results We have recently demonstrated that the murine allantois vascularizes via vasculogenesis, an intrinsic process in which mesoderm is transformed into the endothelial cell lineage in situ, rather than by angiogenesis, which is the extension of blood vessels formed elsewhere (K. M. Downs, et al., supra, 1998). Further, unlike all other vasculogenic systems heretofore described (reviewed in W. Risau and I. Flamme, *Ann. Rev. Cell Dev. Biol.* 11:73–91, 1995), allantoic vasculogenesis is not accompanied by erythropoiesis, i.e., formation of red blood cells.

In the course of our studies, we demonstrated that when allantoises are removed from headfold-stage conceptuses (approximately 8.0 days postcoitum) and cultured under relatively simple conditions in isolation, they rapidly undergo reproducible and stereotypic vasculogenesis (K. M. Downs, et al., supra, 1998). With feeding, the allantoic vasculature is maintained and remodeled for up to 3 days. The cultured explants consist of at least three cell lineages, endothelial, mesothelial, and mesenchymal, all of which are normally found in intact allantoises. Further, correct topographical relations between at least two of these lineages, the endothelial and mesothelial cells, are maintained in the explants. Moreover, cells from explanted cultured allantoises can be returned to developmentally-equivalent host allantoises where they correctly colonize appropriate cell types. Lastly, one of the explanted cell populations, the mesenchyrnal cells, can take up and express exogenous DNA. On the basis of our findings, we propose that the murine allantois will be a powerful and extremely valuable model system for at least two novel applications (Method 1 and Method 2), described below:

Method 1. Evaluation of Potentially Harmful/beneficial Substances on Formation of Blood Vessels During Vasculogenesis In one embodiment of the present invention, allantoic explants will be used to evaluate the effect of potentially toxic environmental compounds and specific gene products on either abrogation or enhancement of blood vessel formation.

Two preferred methods are envisioned to achieve this goal: (a) direct application of a test compound to the cultured allantoic explants or (b) DNA uptake and expression of a test compound by the mesenchymal cells of allantoic explants. We envision that the allantoic explants will, preferably, be created as described below.

In general, allantoises are mouth-aspirated into a hand-pulled glass microcapillary (K. M. Downs and R. L. Gardner, supra; K. M. Downs, et al., supra, 1998) and either cultured in suspension (K. M. Downs, et al., supra, 1998) or placed individually either into wells of 24-well tissue-culture plats (Falcon 304), or onto glass cover slips (12 mm, Fisher) inserted into wells of 24-well tissue-culture plates and coated for 30 minutes in filtered (0.45 $\mu$m, cellulose acetate) poly-D-lysine (1 mg/ml double processed tissue culture water; Sigma) and rinsed 3–4 times with sterile water.

Allantoises are then cultured in 0.5 ml of culture medium (Dulbecco's modified Eagle's medium (DMEM) containing either (i) equal parts of immediately-centrifuged and heat-inactivated rat serum as previously described (K. M. Downs and R. L. Gardner, supra, 1995), or (ii) varying concentrations of heat-inactivated rat or fetal calf serum (the latter obtained from Gibco-BRL; frozen and thawed twice before using). For culture longer than one day, allantoises are given completely fresh medium at 24-hour intervals.

At the onset of culture, or at varying times thereafter, known test compounds, such as Vascular Endothelial Growth Factor (VEGF, R & D Systems, Minneapolis, Minn.), are prepared according to the manufacturer's instructions and added to the cultures in concentrations recommended by the manufacturer (e.g., 1–20 ng VEGF/ml culture medium) or, in the case of unknown test compounds, in varying concentrations to determine the one that either inhibits or enhances vasculogenesis.

The advantage of technique (a) is that a controlled amount of substance can be delivered to the allantois at specific and different times in vascular development and its effect on vascularization assessed. Moreover, that compound can be removed at particular times in order to assess the long-term affect of the compound on the formation of blood vessels.

For technique (b), one would preferentially begin by culturing individually-plated headfold-stage allantoises for 12 or 18 hours in 24-well dishes before transfection, at which time 0.5 ml of heat- and gas-equilibrated DMEM containing 5% fetal calf serum (Gibco-BRL) replaces the culture medium. Allantoises are transfected using a standard $CaHPO_4$ method (F. L. Graham and A. J. van der Eb, *Virology* 54:536–539, 1973) for 6 hours in 5.0% $CO_2$ at 37° C. by addition of 50 $\mu$ of precipitate containing, for example, 1 $\mu$g of plasmid containing the test gene of interest whose expression is driven by the immediate early promoter of human cytomegalovirus (Clontech, Palo Alto, Calif.). Controls are explants cultured in either DMEM containing 50% rat serum or 5% FCS for the 6 hour transfection period. Following incubation, allantoises are washed once with warm PBS and returned to incubate for varying periods at 37° C. in 6.2% $CO_2$ in DMEM containing 50% rat serum to assess the affect of the test compound on vascularization. Expression of the gene of interest is monitored by immunohistochemistry.

The advantage of technique (b) is that, for compounds with relatively short half-lives, the mesenchymal cells of allantoic explants can take up the gene whose product is of interest and express that product continuously in the culture to assess its affect on growth, development and/or maintenance of the vasculature.

Vascular Endothelial Growth Factor (VEGF) is expressed in the allantoic mesothelium (D. J. Dumont, et al., *Dev. Dyn.* 203:80–92, 1995) before spreading into the core (K. M. Downs, unpublished data). We have demonstrated that culture of allantoic explants in high rat serum (20–50% rat serum) is optimal for the formation of blood vessels. Culture of explants in low serum (fetal calf serum, FCS, 5–10%) favors formation of angioblasts, as revealed by expression of Flk-1 and Flt-1, early markers of angioblasts, but not their conversion into nascent blood vessels. Moreover, despite feeding, allantoises cultured in 5% FCS are typically devoid of vascular channels by 48 hours. By 72 hours, explants cultured in and fed 5% FCS at 24 hour intervals consist predominantly of mesenchymal cells. Increasing the concentration of FCS to 10–20% FCS results in partial maintenance of vascular channels for up to 72 hours, though significant breakdown of the channels is observed in about 87.5% of explants. Thus, a high concentration of some factor(s) must be required for both formation and maintenance of endothelial cells in allantoic explants. To test that possibility, recombinant VEGE (1–10 ng/ml culture medium) was added to explants at the start of culture in 5% FOS. Feeding at 24 hour intervals in the presence of Vascular Endothelial Growth Factor (2–10 ng/ml) resulted in formation of many vascular channels containing Flk-1 and Flt-1, and cell survival (78% cell retention compared with 36% in untreated explants) whereas untreated explants or those treated with 1 ng/ml of VEGF were devoid of such channels.

Together these findings suggest that varying the culture conditions of allantoic explants through serum starvation or enrichment varies the state of the endothelial cells, with low serum favoring formation of non-epithelialized angioblasts, and high serum favoring formation of endothelial channels. At least one of the key growth factors required in formation and maintenance of vascularity appears to be VEGF.

Method 2. Amelioration/elimination of Developmental Defects Through Delivery of Blood-borne Therapeutic Factors into the Umbilical Circulation by Formation of Chimeric Allantoises In another embodiment, the present invention is the delivery of factors into the umbilical circulation by formation of a chimeric allantois. Preferably, this delivery results in a therapeutic effect or the amelioration or elimination of developmental defects.

I have recently proposed that cultured allantoic cells may be a valuable source of genetically-manipulable cells that could be re-introduced into developing allantoises where they would express a therapeutic gene and deliver it to the fetal bloodstream for the amelioration/cure of certain developmental defects (K. M. Downs, supra, 1998). We have recently demonstrated that cells of cultured explanted allantoises can be returned to the nascent umbilical cord where they integrate into all three allantoic cell lineages, endothelium, mesothelium and mesenchyme. At least 34% of injected cells colonize the host allantois. In addition, 5.5–6.0% of mesenchymal cells in allantoic explants are able to take up and express exogenously introduced DNA. Mesenchymal cells are thought to be relatively undifferentiated. Then, following transfection of mesenchymal cells with therapeutic genes expressed from appropriate endothelial cell promoters, we propose that donor mesenchymal cells will be introduced into the developing allantois of a developmentally-compromised fetus and, once integrated into the vasculature, they will express the therapeutic compound and deliver it directly into the bloodstream of the affected fetus.

The following is a preferred method of the present invention: Individually-plated headfold-stage allantoises are cultured for 12–18 hours in 24-well dishes before transfection at which time, 0.5 ml of heat- and gas-equilibrated DMEM containing 5% fetal calf serum (Gibco-BRL) replaces the culture medium. Allantoises are transfected using a standard CaHPO4 method (F. L. Graham and A. J. van der Eb, supra, 1973) for 6 hours in 5.0% $CO_2$ at 37° C. by addition of 50 $\mu$l of precipitate containing the plasmid of interest driven either by the immediate early promoter of human cytomegalovirus or the TIE1 endothelial cell specific promoter (Korhonen, et al., *Blood* 86:1828–1835, 1995; T. M. Schlaeger, et al., *Development* 11:1089–1098, 1995). Following incubation, allantoises are washed once with warm PBS and returned to incubate for 20–24 hours at 37° C. in 6.2% $CO_2$ in DMEM containing 50% rat serum. Antibodies to the gene product of interest are applied to some of the cultures to ensure that transfection has taken place and that the gene of interest is being expressed.

Transfection is the process of macromolecule transfer to cells by physical or chemical means. One may decide to use various methods of transfection in the method of the present invention. For nearly twenty years, physical, chemical and viral-based methods have been widely available for introducing DNA into mammalian cells in culture. Physical methods may employ high-voltage electric pulses to create pores in membranes ("electroporation"; E. Neumann, et al., *EMBO J.* 1:841–845, 1982) or a gun to "shoot" genes into individual cells. Most commonly, chemical methods such as calcium phosphate or DEAE-dextran (or its analogues) are used as carrier to deliver DNA into cells (F. L. Graham and A. J. van der Eb, supra, 1973); alternatively, cationic liposomes containing DNA within them fuse with cell membranes to deliver DNA (J. P. Behr, et al., *Proc. Natl. Acad. Sci. USA* 86:6982, 1989; J. P. Loeffler, et al., *J. Neurochem.* 54:1812–1815, 1990; F. Barthel, et al., *DNA Cell Biol.* 12:553, 1993; J. S. Remy, et al., *Bioconjugate Chem.* 5:647–654, 1994). Virus-mediated transfer involves host-specific viruses that either replicate and express DNA in the cytoplasm as episomes (e.g., adenoviruses) or that integrate into the host's genome (e.g., retroviruses).

In the present invention, transfection by calcium phosphate and cationic liposomes (lipofection) will be the two methods of choice used to determine uptake and efficiency of DNA transfer to cultured allantoic cells. These are the most reliable, cost-efficient, and safe means by which to introduce DNA into mammalian cells. However, virus-based transfer is also suitable.

Calcium phosphate precipitation (F. L. Graham and A. J. van der Eb, supra, 1973; M. Wigler, et al., *Cell* 16:777–785, 1977) and lipofection (J. P. Behr, et al., supra, 1989; J. P. Loeffler, et al., supra, 1990; F. Barthel, et al., supra, 1993; J. S. Remy, et al., supra, 1994; Delaplace, 1991) have both been described and reliable and practical kits for both of these methods are available (e.g., ProfectionR Mammalian Transfection Systems and TfxTM products, Promega, Fitchburg, Wis.). Our overall strategy for transfection will involve a timecourse, i.e., application of the reporter gene between the time of removal of the allantois from the conceptus and up to 24 hours in culture.

Calcium phosphate-mediated transfection involves mixing DNA directly with $CaCl_2$ and a phosphate buffer to form a precipitate that is added to the cultured cells. This method achieves both transient and stable expression of DNA, the latter following integration of the transfected DNA into the host cell genome (M. Wigler, et al., *Cell* 16:777–785, 1979; M. Botchan, et al., *Cell* 20:143–152, 1980; S. Kato, et al., *Mol. Cell. Biol.* 6:1787–1795, 1986) or by autonomous replication in mini-chromosomal structures (D.H. Hamer, et al., *Cell* 17:725–735, 1979; D. DiMaio, et al., *Proc. Natl. Acad. Sci. USA* 79:4030–4034, 1982; R. Reeves, et al., *Nucl. Acids Res.* 13:3599–3615, 1985). As described above, allantoises will be removed and plated in individual wells of 24-well tissue culture dishes. One or more allantoises will be plated per well. Because CaP-mediated transfection requires that cells be 30–60% confluent, allantoises will be cultured for 12 hours, which is ample time for them to flatten out and spread somewhat on the bottom of the dish. Prior to transfection, the culture medium will be changed to medium containing 5% fetal calf serum, and the CaP/GFP complex added to the wells. The cells will be returned to the incubator and exposed to the precipitate for 6 hours, after which they will be washed with phosphate buffered saline (PBS, Sigma) and exposed to fresh media. They will then be re-fed every 24 hours up to the time of analysis, which will take place 36–54 hours after transfection (54–72 hours total time in culture) To increase the efficiency of transformation, some of the available "shock" methods, such as application of DMSO, will be applied to the cell cultures 14–16 hours after transfection and immediately removed and replaced with fresh medium.

Delivery of DNA into the nucleus of allantoic cells via lipofection involves close association of the cationic liposome-DNA complex with the cell membrane, followed by internalization of the complex into the cell, perhaps by fusion with the cell membrane and endocytosis (X. Gao and L. Huang, *Gene Ther.* 2:710–722, 1995; P. Hug and R. G. Sleight, *Biochim. Biophys. Acta* 1097:1–17, 1991). This method results in both transient and stable transfection. GFP-plasmid (as a control) and a plasmid of interest will be combined with lipofection reagents (e.g., TfxTM reagent, Promega, Fitchburg, Wis.) according to the manufacturer's instructions. The complexes will then be added to allantoic cell cultures at different timepoints following removal and plating of the allantois. We will do this in both the presence (10% FCS) and absence of serum. Lipofection in the absence of serum is more efficient, but this may of course be, cell line dependent. The advantage of this method of delivery is that two hours, instead of six, is all the time needed to expose cells to the exogenous DNA.

It is possible that chemical methods will not achieve the highest frequency of transfection and expression in whole allantoises. In that case, alternative strategies may be used, which employ viral-mediated DNA transfer. Infection with viruses would be preferred over microinjection of DNA into the nucleus because the latter method is labor intensive and can target only a small number of cells at a time. The general methodology would be similar to that described above for transfection. Allantoises would be plated and soon thereafter infected according to standard protocols with a high titer virus genetically engineered with a reporter gene, for example, GFP whose genetic size is suitable for most viral vectors. Scoring would be as described above, and infected cultures trypsinized and introduced into living embryos to assay for appropriate integration into the vasculature and gene expression.

Most viral vectors have common limitations. Among these are the size of the foreign gene that they may accommodate (maximal insert sizes for SV40 and retroviruses are 2.5 kb and 6 kb, respectively), and/or the fact that they may be subjected to rearrangement upon propagation of the viral stock, a serious consideration in the case of adenoviruses (H. Lochmuller, et al., *Hum. Gene Ther.* 5:1485–1491, 1994) and requiring therefore constant monitoring of viral stocks. Another limitation is the cytopathic effect of some viruses, particularly adenoviruses, on the host cell, which limits expression to a relatively short period of time. Finally, the variability in gene expression depends upon many parameters which are not completely clear. Among these are proper translation, processing, and modification of the resulting protein.

The viral vectors of choice will be adenovirus (Karpati, et al., 1996; Yeh and Perricaudet, 1997) and helper-virus-free retrovirus vectors (K. Shimotohno and H. M. Temin, *Cell* 26:66–77, 1981).

Significance and Summary

Use of the murine allantois as a model in vitro system of vasculogenesis will have enormous impact on the study of formation of blood vessels for several reasons. First, abnormalities during the development of two major vascular systems, the heart and circulation, are the leading cause of birth defects (March of Dimes Web Page, 1999). A valuable approach for elucidating the cellular and molecular mechanisms of endothelial cell formation would be the discovery of practical and reproducible in vitro systems of vasculogenesis. Embryonic stem cells from mice (W. Risau, et al., *Development* 102:471–478, 1988; R. Wang, et al., *Development* 114:303–316, 1992; R. L. Gendron, et al., *Dev. Biol.* 177:332–346, 1996; D. Vittet, et al., *Blood* 88:3424–3431, 1996) and avian epiblast (I. Flamme and W. Risau, supra, 1992; I. Flamme, et al., Anat. Rec. 237:49–57, 1993; K. Krah, et al., *Dev. Biol.* 164:123–132, 1994) have been used to this end. A major drawback to these is that differentiation of embryonic stem cells into the endothelial cell lineage is always accompanied by erythropoiesis. The presence of blood cells makes it difficult to determine which factors are essential for vasculogenesis alone. In addition, the types of cells present and their topographical relationships to each other vary from culture to culture, differentiation occurs over relatively long time periods, and the frequency of vasculogenesis/erythropoiesis is typically much lower than 100 percent. Pure cultures of endothelial cells have been isolated but, because most of them have been derived from adult organs (e.g., J. D. Rone and A. L. Goodman, *Proc. Soc. Exp. Biol. Med.* 184:495–503, 1987; L. C. Masek and J. W. Sweetenham, *Brit. J. Haem.* 88:855–865, 1994; K. Uchida, et al., *Am. J. Physiol.* 266:F81–88, 1994; G. Haraldsen, et al., *Gut* 37:225–234, 1995; T. Sakamoto, et al., *Curr. Eye Res.* 14:621–627, 1995; L. K. Christenson and R. L. Stouffer, *Biol. Reprod.* 55:1397–1404, 1996; Q. Yan, et al., *Invest. Ophthal. Vis. Sci.* 37:2185–2194, 1996), they offer little in the way of recapitulating the early steps of vasculogenesis. Second, although vasculogenesis and angiogenesis are typically described as distinct developmental process, it is not known in what way, if any, these processes involve different factors. Angiogenesis, which is the extension of blood vessels from elsewhere, is critical for the growth and metastatic spread of tumors. In the absence of a blood supply, tumor size remains fixed; without access to the vasculature, metastatic tumor cells are denied access to travel about the body. Vascularization of tumors involves the microvasculature, composed of endothelial cells. Comparison of the effect of particular proteins on the formation of endothelial cells via vasculogenesis in the allantoic explants with current models of endothelial cell formation via angiogenesis may lead to the identification of tumor-specific angiogenic proteins (reviewed in R. Auerbach, *Int. J. Radiat. Biol.* 60:1–10, 1991).

Lastly, the ability of allantoic cells to be geneticallymanipulated and to colonize the developing allantois may prove therapeutically valuable for in utero gene therapy in cases where a blood-borne circulating factor might ameliorate or cure certain fetal defects.

EXAMPLES

I. Method of Delivering Therapeutic Molecules to a Fetus
In General

In the following examples, we examine the fate and developmental potency of cells within the murine allantois during gastrulation.

LacZ-expressing headfold-stage (approximately 8 days postcoitium, dpc) allantoises were subdivided into three prosimodistal regions and transplanted in three sites in synchronous non-transgenic host embryos at sites were the fate of cells was largely known: (1) the base of the allantois (called "orthotopic" and "approximate orthotopic" grafts, R. S. P. Beddington, 1981, 1982), (2) the prospective lateral plate mesoderms of the fetus (called "heterotopic" grafts (R. S. P. Beddington, supra, 1982), and (3) the prospective paraxial mesoderm of the fetus ("heterotopic" grafts). The rationale behind partitioning the allantois was that two of the regions appear to have different functions: the tip is involved in chorioallantoic fusion (K. M. Downs and R. L. Gardner, supra, 1995) and the base may induce or protect presumptive primordial germ cells (PGCs) from differentiation (A. McLaren, *Bibthca Anat.* 24:59–66, 1989; A. McLaren, *Andrologia* 24:243–247, 1992). After 23 hours of whole embryo culture (K. M. Downs and R. L. Gardner, supra, 1995) control and operated conceptuses were stained with benzidine and X-gal, prepared for histology, and examined.

When placed into Site (3), none of the allantoic regions contributed to paraxial mesoderm, but all of them colonized the endothelium of the dorsal aorta and surrounding periaortic mesenchyme when placed there and into Site (2). Thus, these results reveal that angioblasts are present in the allantois by the headfold stage.

Further, striking differences were observed in the state of differentiation of donor allantoic cells dependent upon their original location along the allantoic proximodistal axis. Cells in the base of the allantois were relatively pluripotent, contributing additionally to endoderm of the future coelom and surface ectoderm, whereas cells for the allantoic midregion exhibited the greatest vasculogenic potential. Donor allantoic tip cells returned most often to the distal region of the allantois when placed into Site (1), the base of the allantois.

Our data suggest a model of angioblast formation which states that the genetic changes required for transformation of pluripotent mesodermal cells into differentiated angioblasts commence with increasing distance from the subjacent posterior primitive streak.

Lastly, of potential significance was our finding that allantoic cells, in particular basal ones, do not return to the fetus. Thus, the allantois is a self-contained vasculogenic system.

Use of the Pre-umbilical Cord and Derived Cell Lines in Gene Therapy of the Fetus One objective of the present invention is to use the umbilical cord for fetal gene therapy in utero of congenital defects in blood-borne factors. The umbilical blood vessels provide a direct gateway to the fetal circulation and a very attractive and potentially invaluable system for continuous delivery of therapeutic factors to the fetus.

Although the ultimate goal of this invention is to treat human fetuses with congenital defects in utero, for ethical and practical reasons, the soundness of the approach will first be demonstrated in an animal model. The mouse was chosen for this work because of the similarity of its umbilical cord to the human's, because the murine embryo can be manipulated both ex utero (K. M. Downs and R.L. Gardner, supra, 1995) and in utero (V. E. Papaioannou, In utero manipulations, *In Postimplantation Mammalian Embryos, A Practical Approach*, eds. A. J. Copp and D. L. Cockroft, Oxford: Oxford University Press, 1990), and because the ease of manipulation of the mouse genome has provided excellent models of human genetic disease.

These results suggested that with little manipulation, the native umbilical cord might be an ideal vehicle for delivery of therapeutic substances to developmentally-compromised fetuses.

Delivery of Therapeutic Substances to the Fetus: The Test Model.

The success of our microsurgery in living conceptuses described above has led to the hypothesis that the umbilical cord can be manipulated for therapeutic purposes (see also K. M. Downs and R. L. Gardner, supra, 1995). These results, and others which have demonstrated gene expression from endothelial cell-specific promoters (J. Korhonen, et al., supra, 1995; T. M. Schlaeger, et al., supra, 1995) suggest to me that the umbilical cord has the potential to express therapeutic factors in the endothelial cells that comprise its blood vessels and deliver them to the fetal circulation.

We propose to first demonstrate the present invention in transgenic mice with Haemophilia A. Our ultimate goal is to eliminate antibody production against Factor VIII in human patients with Haemophilia A. Haemophilia is the most common of the inherited bleeding disorders. It affects 1 in 5–10,000 males in all populations and is caused by a defect in clotting Factor VIII. Factor VIII has been cloned and is expressed in many cell types, including mouse fibroblast cells (J. N. Lozier and K. M. Brinkhous, *JAMA* 271:47–51, 1994). There is no precise regulation of the clotting proteins, and no tissue-specific requirement (D. I. Israel and R. J. Kaufman, *Blood* 75:1074–1080, 1990). Because many patients with Haemophilia A will develop inhibitors against recombinant Factor VIII (L. Bi, et al., *Nature Genetics* 10:119–121, 1995), a possible means for preventing formation of these antibodies would be to begin therapy in utero, as the immune system is developing. This would ensure that Factor VIII is not recognized as a foreign protein when given after birth. At present, the only methods available for introducing the fetus to therapeutic factors are the mother's circulation or intermittent injection into the umbilical cord. However, Factor VIII will not cross the placental barrier (V. Mahnovski and Z. Pavlova, *In Diseases of the Fetus and Newborn: Pathology, Radiology, and Genetics*, eds. G. B. Reed, A. E. Clareaux, and A. D. Bain). St. Louis: The C. V. Mosby Company, pp. 417–440, 1989), and injection into the umbilical cord is impractical (half-life of Factor VIII protein is 10 hours, G. G. Brownlee, Prospects for gene therapy of Haemophilia A and B, *In Gene Therapy* (eds. A. M. Lever and P. G. Goodfellow), New York: Churchill Livingstone, 1995) and costly. All of these characteristics make Haemophilia A an excellent candidate disease for the gene therapy of the present invention.

i. Overall Experimental Design

The success of fetal gene therapy via the umbilical cord rests upon obtaining allantois cell lines whose properties are similar to intact allantois cells and which can be manipulated to express therapeutic genes of interest. For this, allantoises from transgenic mice that express β-galactosidase (LacZ) in all their cells (G. Friedrich and P. Soriano, supra, 1991) will be removed and placed in culture. Explants and their LacZ-expressing cells will be selected and infected with a retrovirus containing human Factor VIII (D. I. Israel and R. J. Kaufman, supra, 1990). These LacZ/Factor VIII-expressing cells will then be introduced into the exocelomic cavity of mice defective in Factor VIII (L. Bi, et al., supra, 1995). The fetuses will be monitored through gestation for production of Factor VIII in their serum and antibodies against Factor VIII (L. Bi, et al., supra, 1995). A schematic diagram of the overall experimental design is shown in FIG. 2.

ii. Construction of Factor VIII under Endothelial Cell-Specific Promoters in a Retroviral Vector Factor VIII is produced in the liver, though its exact site of production is still controversial (J. E. Sadler and E. W. Davie, In *The Molecular Basis of Blood Diseases*, 2nd Edition, eds. G. Stamatoyannopoulos, A. W. Nienhuis, P. W. Majerus, and H. Varmus, WB Saunders Co.: Philadelphia, 1994), and its mRNA has been detected in extra-hepatic tissues such as the spleen, lymph nodes, and kidneys (G. G. Brownlee, *In Gene Therapy*, eds. A. M. Lever and P. G. Goodfellow, New York: Churchill Livingstone, 1995). In the liver, Factor VIII is processed in the ER and Golgi, where proteolytic cleavage produces a heavy and light chain held together by metal ions. The Factor VIII heterodimer is then secreted as a glycoprotein into the blood, where it circulates as a complex with von Willebrand factor, itself a multimer. Although Factor VIII requires the presence of von Willebrand factor for stability (G. G. Brownlee, supra, 1995), previous studies have revealed that the endothelial cells of the umbilical cord are a principal producing cell of von Willebrand factor (D. Dickek and T. Quertermous, *In vitro Cell and Dev. Biol.* 25:389–292, 1989). Therefore, Factor VIII should be stable in the system proposed here, as the chimeric umbilical cord will express both Factor VIII and von Willebrand factor. The Factor VIII/von Willebrand complex has a half-life of only about 10 hours. Very low levels of Factor VIII are required for hemostasis (0.1–02 μg/ml vs. 5 μg/ml Factor IX) (G. G. Brownlee, supra, 1995).

Both mouse and human Factor VIII have been cloned and expressed in many cell types (V. Mahnovski and Z. Pavlova, supra, 1989). Factor VIII will be expressed from endothelial cell-specific promoters, either tie-1 (J. Korhonen, et al. supra, 1995) or tie-2 (T. M. Schlaeger, et al., supra, 1995) in a retroviral vector defective in replication (R. G. Vile and S. J. Russell, *In Gene Therapy*, eds. A. M. Lever and P. G. Goodfellow, New York: Churchill Livingstone, 1995). These retroviruses will also carry a selection marker, possibly neomycin, thymidine kinase, metallothionein or adenosine deaminase (Ada) in order to select against uninfected cells. Infection of LacZ-allantois cells with retrovirus containing Factor VIII will be either in whole allantois explants or in cell lines derived from the explants (see next section). Infected allantois cells will be subcloned and duplicated in order to test for (i) LacZ expression, (ii) karyotype, and (iii) expression of Factor VIII protein by the COATEST (D. I. Israel and R. J. Kaufman, supra, 1990). Different cell lines will be compared for the highest production of Factor VIII.

iii. Creation of LacZ/Factor VIII-Expressing Cell Lines

LacZ-expressing and LacZ/Factor VIII-expressing allantois cell lines will be created. LacZ cells express β-galactosidase activity that can be visualized with the application of X-gal, turning the cells blue. Thus for the pilot experiments proposed here, we will be able to monitor the behavior of our cell lines when introduced into living embryos.

Whole allantoises from LacZ-expressing conceptuses will be removed with glass capillary pipettes (K. M. Downs and R. L. Gardner, supra, 1995; K. M. Downs, et al., *Nature*, submitted, 1996) and placed into tissue culture dishes. At first, media containing 15% fetal calf serum will be used, but upon passage, that amount will be reduced to 10% (R. I. Freshney, *Culture of Animal Cells. A Manual of Basic Technique*, New York: Alan R. Liss, Inc., 1983). The following parameters will be varied in order to obtain primary cultures: disaggregation/no disaggregation of the whole allantois before explanting to a tissue culture dish, culture media, dish matrices and stage of allantois removal from the conceptus. Ideally, outgrowths from younger allantoises would be most desirable, as young allantoises are more likely to contain cells that are stem-cell-like. Also, it would be most desirable to obtain a cell line with a normal karyotype (i.e., 40 chromosomes) because such cells should behave normally when eventually re-introduced into the living conceptus.

Once a reasonable number of cells have grown out, they will be passaged and subcloned. Duplicate subclones will be tested for LacZ expression and normal karyotype. Cells expressing LacZ and which have maintained a normal karyotype will be introduced into the exocoelom of a living embryo and assessed for integration into the umbilical cord after appropriate growth of the "operated" conceptus in culture.

If we are unable to obtain karyotypically-normal primary cultures of LacZ/Factor VIII-expressing allantois cells, we will attempt to immortalize allantois cells by introducing explants to replication-defective retroviruses which express SV40 large T antigen, known to immortalize many different cell types in vitro (M. Noble, et al., *Transgenic Research* 4:215–225, 1995) and a selectable marker different from the one used with Factor VIII. Different cell lines will then be introduced into host conceptuses to test for normal behavior and manipulated with Factor VIII as described below.

Infection of cells with a retrovirus carrying Factor VIII will take place either when explants are fairly large (approximately one week) or when a LacZ-allantois cell line has been obtained. Ideally, they will be infected with a defective retrovirus containing Factor VIII and a selectable marker, either neomycin, thymidine kinase or adenosine deaminase (see below). Twenty-four hours after infection, explants will be disaggregated and passaged until cells reach confluence.

iv. Formation of Chimeric Umbilical Cords in utero and Delivery of Factor VIII to Hemophilic Fetuses The second set of experiments will be carried out in utero (V. E. Papaioannou, supra, 1990) in transgenic mice deficient in Factor VIII (L. Bi, et al., supra, 1995). Haemophilia is an X-linked disease, so only about half the males of the litters from the mating $(X+X^H \times X+Y)$ will be defective in Factor VIII. LacZ-/Factor VIII-expressing allantois cell will be introduced into the exocoelom in all implantation sites and become incorporated into the native allantois. These chimeric allantoises will develop into the mature umbilical cord, in which a large portion of donor endothelial cells will express Factor VIII. Because the endothelial cells of blood vessels are very long-lived, Factor VIII will be delivered continuously to the fetal bloodstream throughout gestation.

Because the umbilical cord will be shed at birth and will be the only source of Factor VIII in this experimental design, fetuses must be examined for the presence of Factor VIII before birth. Because we will have no way of knowing which fetuses are the hemizygous affected males, all littermates will be examined. The Factor VIII gene that is eventually introduced into the allantois cells will be engineered in such a way that hemizygous males carrying the mutation in Factor VIII can be distinguished from normal and heterozygous littermates who will not be affected by mutated Factor VIII. This strategy has previously been described (L. Bi, et al., supra, 1995).

All fetuses from every operated litter will be removed from their mother at approximately 18 days postcoitum and tested for the following: (i) Levels of Factor VIII in fetal plasma by the COATEST, (ii) Presence of the defective gene in genomic DNA, and (iii) antibodies against Factor VIII.

At birth, the recombinant allantois cells will be shed with the placenta. Continued therapy with Factor VIII after birth should permit Factor VIII to be recognized as "self" by the adult immune system.

V. Transplantation of Allantoises in the Fetal Liver

For our therapy to reach its full potential, it would be most desirable if allantois/umbilical cells had the potential to colonize fetal/adult organs. In that way, Factor VIII therapy could be continued after birth.

Liver cells are the site of Factor VIII synthesis (G. G. Brownlee, supra, 1995; J. E. Sadler and E. W. Davie, supra, 1994). Thus, in initial experiments, LacZ-expressing allantoises will be introduced into fetal and adult livers, which will then be cultured as whole organ explants (I. Parsa and L. Flancbaum, *Dev. Biol.* 46:120–131, 1975; P. P. L. Tam, *In Postimplantation Mammalian Embryos. A Practical Approach*, Oxford University Press, Oxford, 1990). After suitable culture, explants will be examined for LacZ-expressing cells. If they are found, then genetically-engineered allantois cells expressing LacZ/Factor VIII will be introduced into the fetal liver in utero (V.E. Papaioannou, supra, 1990). In utero, the liver is clearly identifiable as a bright red tissue in the trunk of the fetus. If the allantois cells survive transplantation and express genetically-engineered Factor VIII as MRNA distinguishable from native Factor VIII, then trials will take place in which LacZ/Factor VIII cells will be introduced in utero into litters from matings between heterozygous defective females and normal males (X+X$^H$×X+Y). Newborn pups will be tested for rescue by allantois/umbilical cord cells as previously described (Li, et al., supra, 1995), and for genotype, liver chimerism, and expression of genetically-engineered Factor VIII.

Materials and Methods i. Mouse Strains

The LacZ transgene of ROSA26 (G. Friedrich and P. Soriano, supra, 1991) was made hemizygous on the C57BL/6 (BL/6) genetic background by backcrossing ROSA26 lacZ/+hemizygotes to BL/6 for 8 generations (generous gift of Dr. K. Gould and Professor W. Dove, University of Wisconsin—Madison Medical School). Hemizygous lacZ/+BL/6 males and females were subsequently intercrossed to obtain homozygous lacZ/lacZ BL/6 females. Females were judged homozygous if they transmitted the transgene to all of at least 15 progeny. At n=15, the probability that at least one parental female is lacZ/+ is equal to 0.003 (Professor Robert Wardrop, UW-Madison, Department of Statistics). Homozygous lacZ/lacZ BL/6 females were then crossed with male mice of the CBA strain (Jackson Laboratories). Hemizygous lacZ/+ males and females (both now (BL/6×CBA) were subsequently intercrossed to obtain a homozygous breeding strain, designated ROSA26* of genetic background (BL/6×CBA). Donor embryos for all experiments were obtained by mating F1 hybrid females ((C57BL/6×CBA), Jackson Laboratories) with homozygous ROSA26* lacZ/lacZ (C57BL/6×CBA) males. Host embryos were non-transgenic F2's of hybrid F1 (C57BL/6×CBA) matings.

Mice were kept in 12-hour light-reversed conditions (dark period: 13.00—1.00 hours). Pregnant females were sacrificed by cervical dislocation without prior anesthesia, and the uterine horns dissected into PBS.

ii. Removal and Dissection of Conceptuses

Host conceptuses were dissected at 10.00 on the day of the experiment (approximately 7.75 days post coitum, dpc). In most experiments, only neural plate/late allantoic bud and very early headfold-stage conceptuses were selected as hosts (FIG. 1A; K. M. Downs and T. Davies, supra, 1993; K. M. Downs and R. L. Gardner, supra, 1995). This was to ensure that by the time transplantation was carried out several hours later, most embryos would be at the headfold stage. Conceptuses were paired, and the ectoplacental cone of one member of each pair was trimmed with scissor-motion of two 28 g syringe needles. Trimming the ectoplacental cone enabled the identification of each conceptus after transplantation and culture (K. A. Lawson et al., supra, 1991). Pairs of host conceptuses were then placed in culture medium and maintained in the incubator (K. M. Downs and R. L. Gardner, supra, 1995) until transplantation.

iii. Culture of Allantoises in Isolation

Allantoises of lacZ/+ hemizygous genotype were removed through two vitelline sites (see FIG. 3): (1) directly through visible yolk sac blood islands, or (2) through non-blood island tissue slightly distal to the level of the site of insertion of the allantois with the amnion. Individual allantoises were then placed in 0.5 ml of culture medium (K. M. Downs and R. L. Gardner, supra, 1995) and cultured in roller culture for either 24 or 40–43 hours. After culture, each allantois was stained in benzidine for 30 minutes to detect hemoglobin-expressing cells (see Histochemical Analysis, below).

iv. Transplantation

Figure 3:
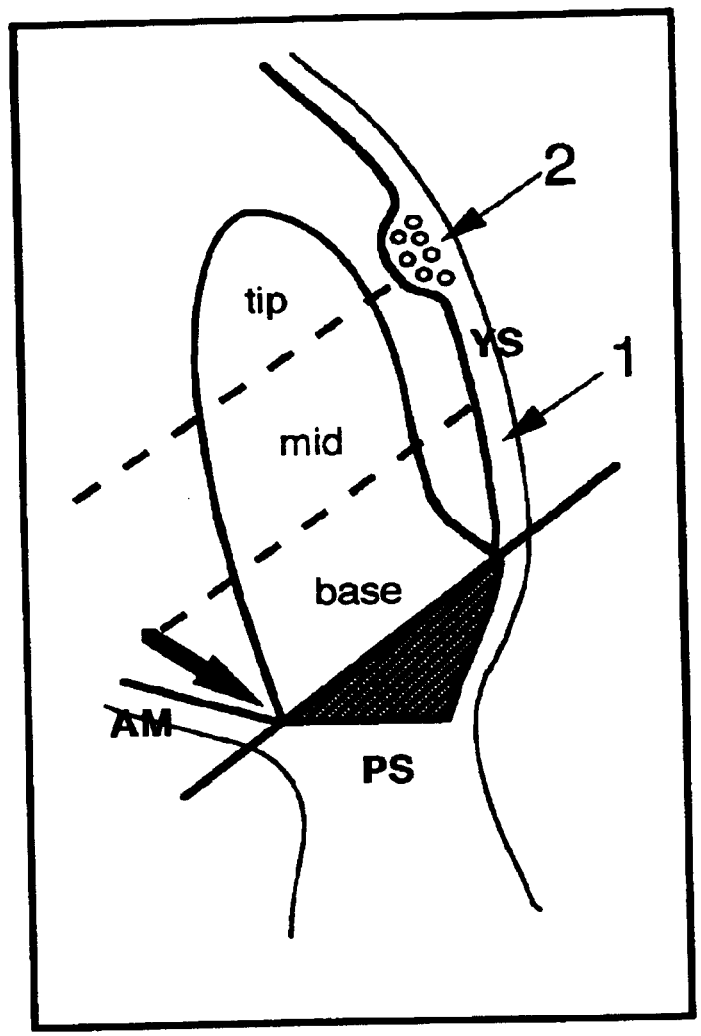
FIG. 3 is a schematic diagram of the allantois and delineation of the base at the level of insertion of the amnion.

Headfold-stage donor allantoises were removed by capillary aspiration by piercing the yolk sac just distal to the site of insertion of the allantois with the amnion (FIG. 3). FIG. 3 is a schematic diagram of the allantois and delineation of the base at the level of insertion of the amnion. The delineation of the base of the allantois with the subjacent primitive streak was determined as the site of insertion of the amnion (arrow). The solid diagonal line indicates the basalmost portion of the allantois taken for this study and its point of separation from the primitive streak (PS) below. The allantois was subdivided into three regions for transplantation (dotted lines): the base, the mid-region and the tip. The numbers 1 and 2 indicate yolk sac sites through which the allantois was removed. Site 1 is typically free of blood islands observable at the level of the light microscope whereas Site 2 contains blood islands. Site 1 was the principal site of yolk sac puncture and removal of the allantois for all of the transplantation experiments described. The bold line surrounding the allantois and which is continuous with the yolk sac and amnion represents the mesothelial lining of the exocoelom. The hatched triangle immediately below the base of the allantois may contain PGC precursors (see Discussion). Abbreviations: AM, amnion; PS, posterior primitive streak; YS, yolk sac.

The basalmost portion of the allantois was taken as the site of insertion of the amnion (W. Ozdzenski, *Zoologica Poloniae* 17:367–381, 1967). Allantoises in which basal cells were not sufficiently removed from attachment to the posterior streak after allantoic aspiration were discarded. Whole allantoises which exhibited distinct basal and distal regions were then rinsed in PBS, and placed individually in trypsin/pancreatin for 5 minutes on ice (B. Hogan, et al., *Manipulating the Mouse Embryo. A Laboratory Manual*, 2nd ed., Cold Spring Harbor Press, Cold Spring, N.Y., 1994), after which the tip, middle third, or base was excised using glass needles (R. S. P. Beddington, "Isolation, culture and manipulation of post-implantation mouse embryos," In *Mammalian Development: A Practical Approach*, (ed. M. Monk), Oxford:IRL Press, 1987; FIG. 5). Donor tissue from the embryonic regions included both epiblast and primitive streak but not visceral endoderm.

Figure 4:
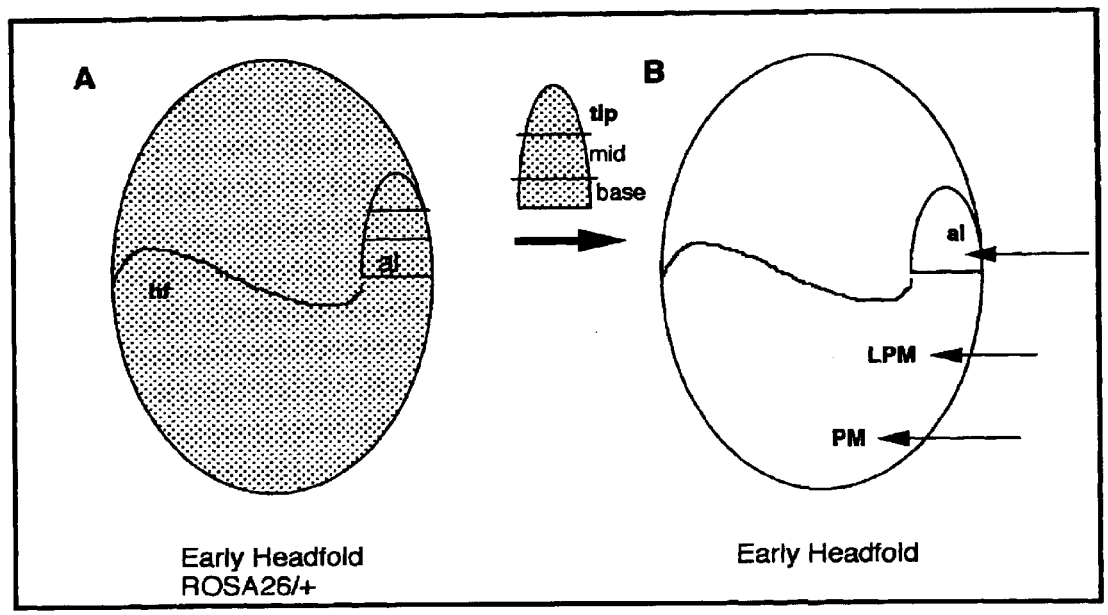
FIGS. 4A and B diagrams sites of transplantation.

Transplantations were carried out either as a series of orthotopic grants only, or as a series of heterotopic grafts which also included a second set of control orthotopic grafts to the base of the allantois. The following host sites were targeted: (1) the base of the allantois, (2) the mid-primitive streak at the level of prospective lateral plate mesoderm, and (3) the more anterior primitive streak at the level of prospective paraxial mesoderm (FIG. 4). Transplantations of the mid- and distal allantoic regions to the base of the allantois were not strictly orthotoic, and therefore they were called "approximate orthotopic" grafts. The point of grafting into the allantois was to control for contribution to the allantois in all experiments where allantoic tissue was placed into the fetus.

Every experiment included unoperated conceptuses and several unoperated transgenic conceptuses in order to compare the extent of development between donor and host embryos (see Morphology of Cultured Conceptuses, below), and to ensure appropriate benzidine and X-gal staining (see Histochemical Analysis). At the time of transplantation, donor tissue was placed in a drop of dissection medium on a glass slide from which the single chamber was removed, leaving behind a silicon gasket (Nunc). The tissue was then cut further into clumps of approximately 10–30 cells; every effort was made to inject all fragments from the desired region; this was successful most of the time. Pairs of recipient conceptuses to be injected were placed in a second drop of dissection medium. Transplantations were carried out in a Nikon Diaphot inverted microscope with bright-field and DIC optics.

Two Leitz micromanipulation arms were used to manipulate holding and microinjection pipettes. Holding pipettes (O.D. 1.00 mm, I. D. 0.75 mm) were hand-pulled and heat-polished (R. S. P. Beddington, supra, 1987) on a deFonbrune microforge to an inner diameter of 0.05 mm. Microinjection pipettes were pulled on an electrode puller (Sutter Instruments, Novato, Calif.), broken to an I.D. of 0.03 mm on the microforge, and heat-polished. Holding and microinjection pipettes were mounted on microelectrode holders (World Precision Instruments) containing either 0.1 M KCl and silicon oil (holding pipettes) or dissection medium and silicon oil (microinjection pipettes). The electrode holders were connected to Hamilton syringes of 500 $\mu$l (holding pipettes) or 100 $\mu$l (microinjection pipettes).

All experimental embryos were photographed at the time of transplantation using a video monitor attached to a tv screen (Sony) and printer loaded with black-and-white heat-sensitive paper (Sony) in order to verify retrospectively initial embryonic stage and the site of injection.

v. Morphology of Cultured Conceptuses

After culture, each conceptus was scored for the following morphological features (N. A. Brown, "Routine assessment of morphology and growth: scoring systems and measurements of size," In *Postimplantation Mammalian Embryos: a Practical Approach*, eds. A. J. Copp and D. L. Cockroft, Oxford:IRL Press, 1990): chorioallantoic fusion, yolk sac circulation, heart beat, turning, extent of development of the gut, brain, heart, and numbers of somite pairs. None of the conceptuses were grossly deficient in any one of these features, but a few exhibited an obvious lack of growth and organization and were judged abnormal (0.65% total cultured conceptuses were not included in the final analysis). The extent of development between unoperated hosts and transgenic conceptuses was also compared in order to verify that the rate of development of donor and host conceptuses was similar. In this analysis, a student T-test revealed no significant differences between development of headfold-stage donor and host conceptuses (scoring based on Brown, supra, 1990; n=18 (lacZ/+), n=38 (+/+); p=0.25, equal variances assumed, C. I.=95.0%).

vi. Histochemical Analysis and Scoring Grafted Cells

After culture, conceptuses and whole allantoises cultured in isolation were immediately stained in benzidine to identify host hemoglobin-synthesizing red blood cells: 20 $\mu$l 30% $H_2O_2$ (Sigma) was added to 1 ml benzidine stock solution (benzidine stock solution: 50 ml 0.5 M glacial acetic acid plus 100 mg benzidine (Sigma)); 100 $\mu$l of the benzidine/$H_2O_2$ mixture was added to 400 $\mu$l phosphate-buffered saline (PBS, Sigma) to produce a working solution. 100 $\mu$l of the working solution was added to 300 $\mu$l dissection medium which contained conceptuses (K. M. Downs and R. L. Gardner, supra, 1995) at room temperature for 15 minutes. Conceptuses and allantoises were then rinsed twice in PBS and fixed for 2–2.5 hours at 4° C. in 4% paraformaldehyde. All cells of ROSA26* lacZ/+ hemizygous donor headfold-stage conceptuses were blue after staining in X-gal, both before and after culture (data not shown), with the exception of an occasional (0.01%) benzidine-positive donor cell (see below). Fixation periods of 5 hours or more compromised the ubiquity of X-gal staining in some cell lineages, particularly yolk sac endoderm, the chorion, and trophoblast giant cells overlying the ectoplacental cone. Fixed conceptuses were rinsed 3 times in PBS (20 minutes each) and stained in X-gal (Sigma) at 37° C. for at least 15 hours (Sanes, et al., supra, 1986). We found that post-fixation in 4% paraformaldehyde after X-gal staining had no visible effect on retention of the X-gal stain. Conceptuses were then examined for the presence of transgenic cells before processing for wax histology by conventional means, which included vacuum at the paraplast embedding step.

Conceptuses were sectioned at 4 $\mu$m thickness (Reichert-Jung Autocut), and the sections dried at 42° C. for at least 7 hours. Slides were dewaxed by conventional means, and counterstained in Nuclear Fast Red (Sigma; MacGregor, et al., *Development* 121:1487–1496, 1995) for 5 seconds to 1 minute before mounting in Permount. Nuclei of transgenic donor cells were counted in every section and locations noted. Operated conceptuses that contained $\geq$5 incorporated cells were scored as chimeric.

Only red blood cells stained pale yellow to deep orange if they contained hemoglobin. When co-stained with X-gal, the overwhelming majority of red blood cells contained significant amounts of X-gal precipitate; some red blood cells contained significant amounts of X-gal precipitate; some red blood cells were speckled blue, and very infrequently (<0.01%), a hemoglobin-positive cell appeared negative. In the absence of benzidine, all transgenic red blood cells stained blue with X-gal.

Results

Figure 6:
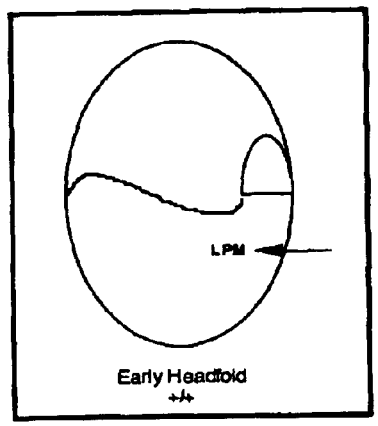
FIG. 6 is a summary of results of grafts into prospective lateral plate mesoderm, headfold stage.

Transplantation was used to determine the developmental potency of the allantois. Donor allantoises of hemizygous lacZ/+ genotype were subdivided into three regions (FIG. 4): base, middle-third, and tip, and each region was transplanted into three sites in the conceptus: the base of the allantois, the prospective lateral plate mesoderm (LPM) and the prospective paraxial mesoderm (PM) (FIG. 4). These embryonic sites were chosen because they had been previously characterized by transplantation (P. P. L. Tam and R. S. P. Beddington, supra, 1987), and therefore offered the opportunity to compare the developmental potential of allantoic extraembryonic mesoderm in sites where embryonic mesoderm was forming. Most hosts were at the headfold-stage at the time of transplantation, but a small number had reached early somite stages (FIGS. 5–7). After culture, each chimera was examined for the whereabouts of donor allantoic tissue. Benzidine staining, specific for red blood cells containing hemoglobin, facilitated identification of host endothelial cells.

FIG. 5 is a summary of results of grafts of donor allantoic tissue into the base of host allantoises, headfold stage. The results of transplants of the three donor allantoic regions, tip, middle third, and base, into the base of the allantois of host conceptuses are shown for every chimera.

FIG. 6 is a summary of results of grafts into prospective lateral plate mesoderm, headfold stage. The number and location of donor transgenic cells are shown for every chimera 23 hours after orthotopic (same site) and heterotopic grafts of the three allantoic regions were introduced into the primitive streak at the level of prospective lateral plate mesoderm. The initial and final stages of each chimeric conceptus are shown (HF, headfold; ordinal numbers are pairs of somites).

FIG. 7 is a summary of results of grafts into prospective paraxial mesoderm, headfold stage. This figure summarizes the number and location of donor transgenic cells 23 hours after orthotopic (same site) and heterotopic grafts of the three allantoic regions were introduced into the primitive streak at the level of prospective paraxial mesoderm. The initial and final stages are as described in FIG. 6. Abbreviations: MT, middle third of allantois.

Orthotopic Control Transplantations

To obtain a profile of the potentially colonizable tissues for each of the three transplantation sites, a set of five orthotopic experiments was carried out, using similar numbers of conceptuses (Table 1A, below). The number of chimeras obtained at these orthotopic sites was within the range of that previously reported (5–12 chimeras; P. P. L. Tam and R. S. P. Beddington, supra, 1987). Embryos receiving grafts from the base of the allantois exhibited the highest rate of chimerism, whereas those receiving grafts at the level of paraxial mesoderm were least efficiently colonized.

not separate the primitive streak from epiblast as did Tam and Beddington (1987), as we did not know whether the allantois would be able to give rise to derivatives of all three primary germ layers rather than to mesoderm alone.

Orthotopic transplantations of the region of the conceptus giving rise to paraxial mesoderm exhibited the lowest rate of chimerism (33.3%, Table 1A) of all orthotopic grafts. However, this number was not significantly different from

TABLE 1

| Expt Set | Site of Injection | Tissue | No. Expts | No. Embs. Injected | No. Neg. Grafts (%) | No. Grafts Unincorp. (%) | No. Chimeras (%) | Mean No. Grafted Cells ± SEM (Median) | Type of Tissue Colonized |
|---|---|---|---|---|---|---|---|---|---|
| A | O-Base | Base of Allantois | 5 | 20 | 3 (15.0) | 3 (15.0) | 14 (70.0) | 182.6 ± 46.2 (115.5) | allantois |
|   | O-LPM | Prospective LPM | 5 | 19 | 4 (21.1) | 5 (26.3) | 10 (52.6) | 192.5 ± 68.7 (100.5) | multiple |
|   | O-PM | Prospective PM | 5 | 21 | 6 (28.6) | 8 (38.1) | 7 (33.3) | 145.9 ± 61.3 (73) | multiple |
| B | Base of Allantois | Base of Allantois | 4 | 15 | 5* (33.3) | 3 (20.0) | 7 (46.7) | 441 ± 304 (185) | allantois |
|   |   | Middle Third | 4 | 21 | 2† (9.5) | 3 (14.3) | 16 (76.2) | 607 ± 166 (471) | allantois |
|   |   | Tip of Allantois | 4 | 14 | 1 (7.1) | 1 (7.1) | 12 (85.7) | 208.4 ± 82.6 (102) | allantois |
|   | Prospect. LPM | Base of Allantois | 4 | 17 | 7 (41.2) | 6 (35.3) | 4 (23.5) | 697 ± 402 (452) | multiple |
|   |   | Middle Third | 4 | 22 | 3 (13.6) | 7 (31.8) | 12 (54.5) | 230.8 ± 60.0 (175) | endothelia, mesoderm |
|   |   | Tip of Allantois | 4 | 18 | 2 (11.1) | 11 (61.1) | 5 (27.8) | 199.0 ± 139.0 (87) | endothelia, mesoderm |
|   | Prospect. PM | Base of Allantois | 4 | 19 | 7 (36.8) | 10 (52.6) | 2 (10.5) | 68.0 ± 48.0 | endothelia, mesoderm |
|   |   | Middle Third | 4 | 21 | 7 (33.3) | 8 (38.1) | 6 (28.6) | 176.7 ± 75.7 (130) | endothelia, mesoderm |
|   |   | Tip of Allantois | 3 | 13 | 1 (7.7) | 8 (61.5) | 4 (30.8) | 85.0 ± 43.2 (62) | endothelia, mesoderm |

Table 1 tabulates the frequency of Experimental Chimeras and Mean Number of Grafted Donor Descendant Cells. The bold horizontal lines delineate the types of transplantations carried out in every experiment. In Experimental Set A, orthotopic (O) transplantations were carried out to three sites: the base of the allantois, prospective LPM, and prospective PM. In Experimental Set B, the allantois was subdivided into three regions, tip, middle third, and base. Each of these regions was then transplanted to three sites in the same experiment: base of the allantois, prospective lateral plate mesoderm (LPM), and prospective paraxial mesoderm (PM). Abbreviations: Embs, embryos; Expt., experiments; Neg., negative; No., number; SEM, standard error of the mean. The * symbol indicates that one graft had only four cells incorporated into the allantoic endothelium. The † symbol indicates that one graft had only one cell incorporated into the allantoic endothelium.

Orthotopic transplantations of the base of the allantois were carried out for the first time. These revealed the fate of cells in the base of the allantois. The rate of allantoic chimerism was relatively high compared with the other two transplantation sites (Table 1A). The higher rate of success with the former was likely due to symmetric apposition and greater distance between holding and injection pipettes than used with the other sites. All orthotopically-placed cells from the base of the allantois contributed exclusively to the allantois. None were found in the fetus (FIG. 5A).

Orthotopic grafts of the region of the primitive streak that gives rise to lateral plate mesoderm resulted in colonization of a wide range of different tissues (FIG. 6). Contribution to non-mesodermal tissues likely reflects the fact that we did the overall rate of chimerism for the other two sites. Because transplantations to this site contained a similar number of grafted cells as the other two transplantation sites, the smaller number of chimeras found at the level of prospective paraxial mesoderm is likely explained by destabilization of the injection site due to overlap in the level of the holding and injection pipettes (which, incidentally, we found to be superior than other arrangements of the pipettes at this site). Nonetheless, the number of positive chimeric fetuses was just one less than the number previously analyzed (P. P. L. Tam and R. S. P. Beddington, supra, 1987). Colonization patterns in chimeric embryos included paraxial mesoderm, as previously described (P. P. L. Tam and R. S. P. Beddington, supra, 1987; FIG. 7).

Developmental Potency of the Allantois

Orthotopic and Approximate Orthotopic Transplantation of the Allantois

Given the array of potentially colonizable tissues at each of the three transplantation sites, we then carried out a series of experiments designed to determine the developmental potential of the allantois (Table 2B). Orthotopic and approximate orthotopic transplantations of the allantois were used to verify accuracy of graft placement by demonstrating within each experiment that allantoic cells contributed to the allantois when placed there. In addition, they provided additional data on the fate of the basal allantoic cells, and on the developmental potential of the allantoic mid-region and tip (see below).

When all three allantoic regions were placed into the base of the allantois of a host, grafted allantoic cells were well-incorporated in the allantois and were sometimes distributed amongst two of the three allantoic regions delineated in this study: base, mid-portion and distal third (FIG. 5). Grafted cells were typically well-spread across the girth of the host allantois, as demonstrated by their absence in many consecutive sections.

Of potentially important significance was our finding that when placed into the base of the allantois, donor allantoic cells from all three allantoic regions were conspicuously absent in the fetus, either as integral tissue components or contained within the fetal vasculature. Rather, most donor allantoic grafts contributed cells only to the allantois or, in a minority of cases, to the yolk sac (FIG. 5; see below). Moreover, only 8.2% of all donor grafts contributed cells to the base of the allantois. This observation suggests that normal cell movement within the allantois is from proximal-to-distal. Of the chimeras which contained a few donor cells in the base, colonization by these donor cells was found in the nascent allantoic vasculature (data not shown).

In four chimeras, some donor allantoic cells contributed to the endothelium of the immediately adjacent omphalomesenteric artery (FIGS. 5A, B). However, because the overwhelming majority of grafts contributed exclusively to the allantois (45/49), we believe that contribution to the yolk sac vasculature may have been due to contamination of the yolk sac by grafted cells when the injection pipette was withdrawn from the conceptus, or possibly by displacement of part of the graft to the yolk sac during subsequent culture. This is because in one instance we found a small cluster of unincorporated cells (chimera number 3, FIG. 5B) adherent to the outside of the yolk sac at the level of the site of injection into the base of the allantois.

Some striking and potentially significant differences between the three allantoic regions were also evident from these grafts. In particular, although all three allantoic regions had been placed into the base of the allantois, cells derived from the donor mid-region and tip made significant contributions to the chorioallantoic fusion junction of the host (FIG. 8), with cells from the tip contributing the highest number. In contrast, donor cells from the base of the allantois rarely translocated that far. Also, the base of the allantois contributed the highest percentage of descendants to the allantoic endothelial lineage, and were found predominantly in the host allantoic mid-region (FIG. 8).

Figure 8:
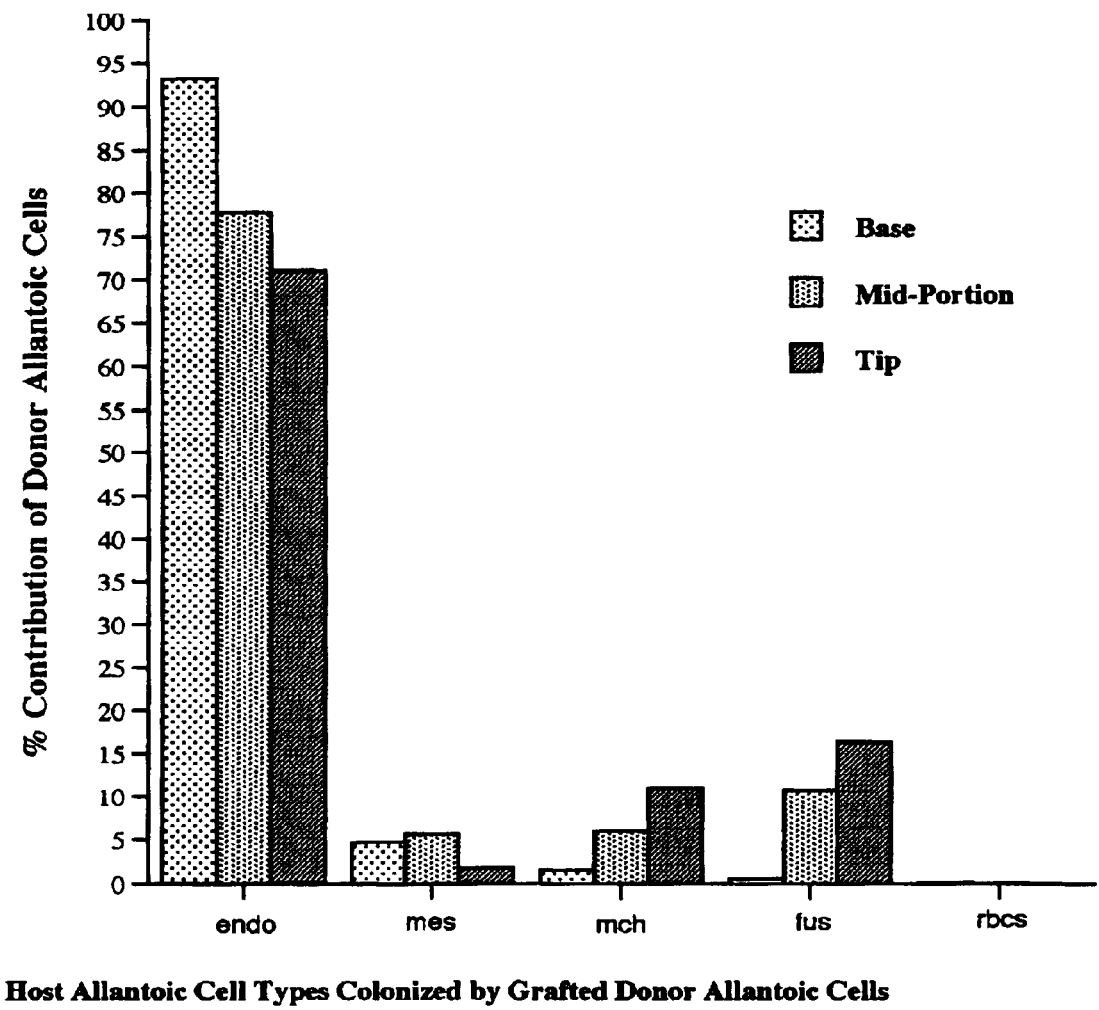
FIG. 8 diagrams colonization patterns by cell type of grafted allantoic tissue into host allantoises.

FIG. 8 diagrams colonization patterns by cell type of grafted allantoic tissue into host allantoises. The colonization patterns of donor allantoic tissue 23 hours after placement into the allantois of host conceptuses. The total number of grafted cells according to donor allantoic region was: base (5613), mid-portion (9538), and tip (2501).

Heterotopic Transplantations of Donor Allantoic Tissue

Prospective Paraxial Mesoderm (PM)

None of the three allantoic regions colonized pre-somitic or paraxial(somitic) mesoderm (Table 5B). In the chimeras obtained from all three donor allantoic regions, donor colonization of the fetus at the level of the prospective paraxial mesoderm was again in the endothelial lining of the dorsal aorta and in mesenchyme adjacent to the dorsal aorta (FIG. 7). The allantoic mid-portion revealed the highest average number of grafted cells, whereas the base and tip contributed relatively few. Nevertheless, most chimeras containing grafts of the allantoic mid-portion also contained clumps of unincorporated tissue, suggesting that not all cells of the allantoic mid-region can colonize this embryonic region. Interestingly, the base of the allantois did not exhibit the relative pluripotency in this region of the conceptus that it did when transplanted into prospective LPM.

Discussion

We have investigated the developmental potential of the extraembryonic mesoderm of the headfold stage allantois. In addition, the fate of cells in the base of the allantois was followed for the first time. Under the conditions used, all fetal and extraembryonic lineages in the LacZ-containing donor conceptuses stained strongly blue upon X-gal staining, both before and after culture, with the exception of a few donor cells of the erythropoietic lineage, due to co-staining in benzidine.

During the headfold stage, the primitive streak has fully elongated from its posteriormost site at the embryonic/extraembryonic junction of the conceptus to the distal tip of the egg cylinder; it is still an active source of mesodermal tissue at this stage (P. P. L. Tam and R. S. P. Beddington, supra, 1987). The developmental potency of the headfold-stage allantois was challenged by placing it into two sites of the primitive streak of synchronous embryos: the mid-portion of the primitive streak where mesoderm emerges as lateral plate mesoderm, and the primitive streak where paraxial mesoderm is formed, just posterior to the node (P. P. L. Tam and R. S. P. Beddington, supra, 1987). In addition, placement of the distal-third of the allantois into the base, originally intended to control for contribution of donor allantoic cells to the allantois in the second set of experiments (Table 4B), provided additional data on the growth and state of differentiation of the headfold-stage allantois.

The Allantois and Embryonic Mesoderm

All three regions of the donor allantois contributed predominantly to the endothelium of the dorsal aorta and adjacent mesenchyme when placed into the fetus. This mesenchyme is thought to be recruited into connective tissue and/or smooth muscle comprising the surrounding tunicae of the mature aorta (Arey, 1966; reviewed in Noden, 1989).

Only the base of the allantois exhibited a greater developmental potential than the other two regions when placed into prospective lateral plate mesoderm, contributing descendants to the endoderm of the future coelom as well as to surface ectoderm and lateral plate mesoderm, similar to the orthotopic control grafts. Thus, the base of the allantois may contain a somewhat more developmentally labile population of cells than the two distal allantoic regions. The relative pluripotency of the base of the allantois is not surprising, given that cells in the base of the allantois are the freshest mesodermal cells to emerge from the posterior streak until the 3-somite stage (P. P. L. Tam and R. S. P. Beddington, supra, 1987), and therefore, they may be the least differentiated.

The fetal lineages colonized by allantoic tissue following placement into the primitive streak at the level of prospective paraxial mesoderm revealed no overlap with the orthotopic control grafts. In particular, none of the regions of the allantois contributed to paraxial mesoderm. This suggests that the allantois share few, if any, properties with presomitic, or paraxial, mesoderm. The base and the tip of the donor allantois exhibited the fewest number of grafted cells per embryo after placement into prospective paraxial mesoderm whereas the mid-region produced the most descendants. This suggests that the environment at this level of the streak cannot support pluripotent basal cells and more specialized tip cells. It further suggests that those grafted cells that have become angioblasts may have the best chance of becoming incorporated into this less "allantoic-favorable" region of the conceptus.

State of Differentiation of the Allantois Along its Proximodistal Axis

Grafts of allantoic tissue into the base of the allantois confirmed that there appear to be significant differences in the state of differentiation along the proximodistal axis of the headfold-stage allantois. This was manifest in the final translocation profiles of the three allantoic regions after placement into the base of a host allantois (FIG. 5). The majority of basal allantoic cells moved only as far as the allantoic midregion. In contrast, the majority of donor cells whose origin was the allantoic mid-region or tip moved further distally. The tip exhibited the largest fraction of cells in the chorioallantoic fusion junction (FIG. 8). This suggests that allantoic tip cells might be specialized for chorioallantoic fusion as early as the headfold stage or that cells destined for the endothelial cell lineage at the fusion junction possess properties different from those in the midregion. Allantoic tip cells probably do not express the entire repertory of genes required for chorioallantoic fusion at the headfold stage, however, because previous studies have shown that the distal half of the allantois is not competent to fuse with the chorion until it has attained developmental maturity, typically at the equivalent of 4–6 somite pairs (K. M. Downs and R. L. Gardner, supra, 1995).

Differentiation of Allantoic Mesoderm into Angioblasts: The Position-Effect Model Previous studies have suggested that all mesoderm has the ability to undergo vasculogenesis, given the correct environment (Pardanaud, et al., 1987; Coffin and Poole, 1988). The heart, large blood vessels and the vitelline vasculature are formed by vasculogenesis, a uniquely embryonic process in which pluripotent mesodermal cells differentiate into angioblasts that subsequently aggregate and assemble in situ into new blood vessels. Angiogenesis, which is the formation of blood vessels from pre-existing ones, occurs once the major vascular systems are in place.

Angiogenesis occurs during both embryogenesis and throughout the life of the organism. Very little is known about how the umbilical vasculature is formed. Electron micrographic analyses of the allantois have not been presented in enough detail to confirm the existence of angiogenic clusters (Tamarin and Boyde, 1977), but Ellington (1985) has described rudiments of the vascular system in the rat by 10 dpc (equivalent to approximately 4-somite pairs in the mouse). Expression studies have also shown that Vascular Endothelial Growth Factor (VEGF), its two receptors, VEGFR1-flt-1 and VEGFR2-flk-1 (Yamaguchi, et al., 1993; Breier, et al., 1995) and TEK (tie-2) (Schnurch and Risau, 1993) are expressed early in the allantois. These suggested that vasculogenesis was occurring in the pre-fusion allantois, but without examination of the developmental fate and potency of allantoic cells, the true significance of these patterns could not be verified.

Our transplantation experiments support the possibility that the umbilical vasculature is formed by vasculogenesis rather than by angiogenesis. This is because allantoic angioblasts were found incorporated in the large vessel endothelium of the dorsal aorta and intersegmental arteries rather than in small capillaries. Although it is possible that the nearby yolk sac contributes endothelial cells to the allantois, making angiogenesis the principal mechanism of formation of the umbilical vasculature rather than de novo vasculogenesis, we have some evidence that this is not the case. Yolk sac transplantations demonstrated that the earliest time at which yolk sac cells move into the allantois is after fusion, at about 10-somite pairs (M. Blahnik, S. Gifford, and K. M. Downs, unpublished data). This is approximately 22 hours after the headfold stage at which the donor allantoises used in this study were removed for transplantation. Also, benzidine staining and cell profiles demonstrated that all of the yolk sac-derived cells within the host allantois appear to be red blood cells.

If angioblasts are formed de novo within the allantois, then how do extraembryonic mesodermal cells that comprise the allantoic bud differentiate into angioblasts? Two lines of evidence produced here suggest that distance of pluripotent mesodermal cells from the posterior streak dictates angioblast differentiation. First, movement within the growing allantois is from proximal to distal. Second, distinct differences in the state of differentiation were discovered along the proximodistal axis of the headfold-stage allantois. Basal allantoic cells were relatively more pluripotent than cells in the distal allantoic region. The allantoic mid-region was most efficient at colonizing the endothelium of the fetus, producing the highest number of chimeras and grafted cell descendants. Cells in the allantoic tip were most efficient at colonizing the chorioallantoic fusion junction.

Figure 9:
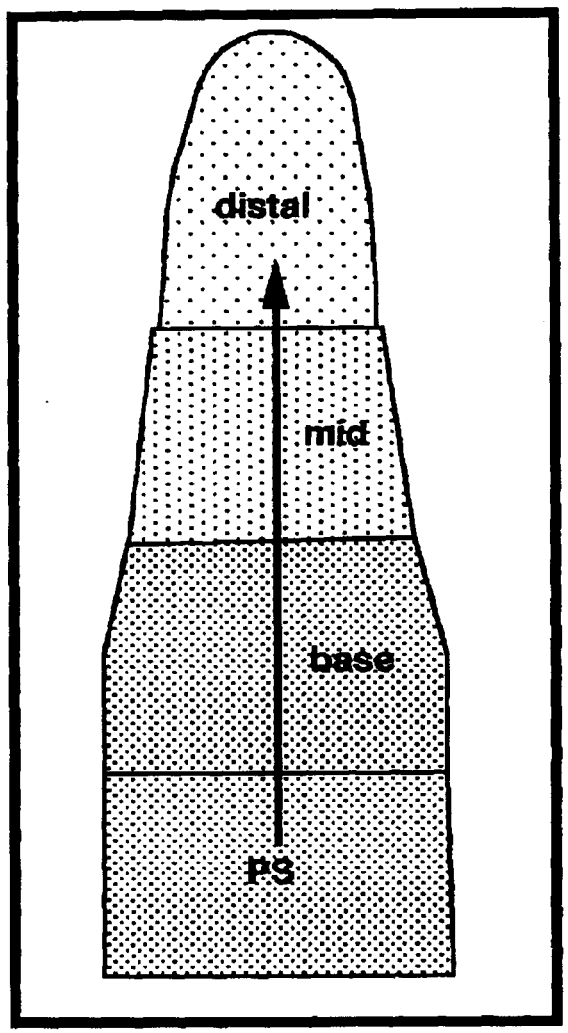
FIG. 9 is a "position-effect" model of angioblast formation in the allantois.

Together, these data suggest that extraembryonic mesoderm destined for the allantois emerges from the primitive streak in a relatively pluripotent state, but as it is pushed distally by sustained addition of nascent extraembryonic mesoderm into the allantoic base, it moves out of the sphere of influence of the primitive streak and differentiates into angioblasts. Movement farther into the tip entails further differentiation, either into allantoic cells specialized in fusion with the chorion or possibly into specialized umbilical endothelial cells. This model, called the "Position-Effect Model" of angioblast formation, is described in FIG. 9.

Position-dependent differentiation has been previously described for the trophectoderm (R. L. Gardner, et al., 1973; Copp, 1978). The distinct fates of mural and polar trophectoderm may be a consequence of their position with respect to the inner cell mass (ICM; R. L. Gardner and R. S. P. Beddington, supra, 1988). Close contact with the inner cell mass results in proliferation of polar trophectoderm and differentiation into extraembryonic ectoderm whereas giant cells are formed when the mural trophectoderm is deprived of contact with the ICM. Then, once a critical distance from the ICM-derived primitive ectoderm is achieved by the polarmost trophectoderm cells, they differentiate into secondary giant cells.

The Base of the Allantois and the Germ Line

Ozdzenski (1967) hypothesized that a small population of alkaline phosphatase-positive cells that resides in the base of the headfold-stage allantois contributes either to the mature allantois, to the germ line or to both. Our experiments represent the first direct attempt to resolve this hypothesis by following the fate of cells in the base of the allantois.

Results presented here suggest that cells in the base of the headfold-stage allantois contribute only to the mature allantois. None of the basal allantoic cells were found in the fetus. That the grafts had ample time to translocate out of the base of the host allantois was demonstrated by the observation that most grafted descendants were found in the distal two-thirds of the host allantois at the end of the culture period.

Thus, these data suggest that the fate of cells in the base of the allantois is to contribute to somatic lineages, e.g., the allantois, rather than to become incorporated into the future germ line (Ozdzenski, 1967). Nevertheless, the possibility that the base of the allantois contains the future germ line cannot be entirely ruled out. One reason is that the triangle of allantoic base/primitive streak had not been used in the transplantations and the germ cells may lie in this small region (FIG. 3). The other is that the germ cells failed to survive transplantation. The latter possibility seems somewhat unlikely, as previous studies have shown that cells taken from this region survive culture and contribute extensively to somatic chimeras (Matsui, et al., 1992). In one instance, these cultured cells even contributed to the germ line (Labosky, et al., 1994). Therefore, definitive proof of the whereabouts of the PGCs before colonization of the hindgut awaits further analysis.

Conclusions

The main function of the allantois is to fuse with the chorion and vascularize, thereby forming the umbilical component of the chorioallantoic placenta. Angioblasts appear almost as soon as the allantois emerges from the posterior primitive streak. Allantoic vascularization is not dependent upon fusion with the chorion (T. P. Yamaguchi, et al., *Development* 118:489–498, 1993; K. M. Downs and R. L. Gardner, supra, 1995). Moreover, formation of the umbilical vasculature does not appear to be dependent upon interaction with endoderm. Our discovery of the whereabouts of pluripotent and differentiated cells within the allantois provides, for the first time, a developmental blueprint essential for understanding the role of genes expressed in the allantois during the headfold-stage. The allantois, heretofore little studied, offers a promising and highly manipulable system to discover how angioblasts are formed from pluripotent mesoderm in the living mammalian conceptus.

Gene Targeting in the Murine Allantois

At the headfold stage of mouse development, angioblasts are present in the allantois. The Examples above describe a technique for culturing and transplanting headfold stage allantoic cells into the allantoises of host embryos. These donor cells incorporate into the developing vasculature. If allantoic angioblasts are genetically manipulable, transplantation of transfected angioblasts could be used for genetic studies of vascular development. This method might also prove useful for providing exogenous gene products for therapeutic uses in developmentally-compromised fetuses.

Mice of a modified ROSA26 strain (ROSA26*), transgenic for the lacZ gene, provided donor material for transplantation. A thin glass capillary punctured the yolk sac, and suction through the capillary was used to remove the elongated allantoises from headfold stage embryos. The removed allantoises were plated in culture medium containing 50% rat serum and remained in culture overnight. An X-gal stained section from a headfold stage embryo of the ROSA26* donor strain demonstrated that all cells of the embryo, including the cells of the allantois, were positive for blue X-gal staining. Overnight cultures of donor allantoises were dissociated and injected into the allantoises of host embryos which had been cultured for 18 hours starting at headfold stage (see FIG. 2). Injected host embryos were returned to culture for a further 8 hours. Injections of the host embryos pierced the yolk sac at the site near the chorion which is free of vasculature.

At the end of the final incubation period, the injected embryos had developed to the somite stage. Eight hours after injection, the injected embryos were fixed in 4% paraformaldehyde. After fixation, embryos were stained with X-gal, embedded in paraffin, and sectioned at 4 $\mu$m. Sections were then dewaxed and stained with nuclear fast red.

Results

Stained slides were examined to detect blue donor allantoic cells within the host embryos. We looked for blue cells on the yolk sac, amnion, fetus, and allantois. Incorporation of donor allantoic cells occurred almost exclusively in the allantois of the host. The incorporated cells appeared as endothelial, mesothelial, and mesenchymal cells.

In examining the allantois, we divided it into four regions, to determine whether the transplanted allantoic cells incorporate preferentially into specific regions of the allantois. The four divisions consisted of: the base region close to the fetus, the mid-region, the distal region nearing the chorion, and the fusion junction, where the allantois is attached to the chorion. The donor cells incorporated into the host allantois predominantly in the distal and fusion junction regions. Very few incorporated into the mid region, and none were present in the base. Although clusters of donor cells did attach to the yolk sac and amnion, these cells did not incorporate into the structure of these membranes and remained attached only to the surface.

Tables 2–4 summarize our findings. Table 2 shows the number of incorporated donor cells found in each region of the host allantois. Table 3 shows the number of incorporated donor cells which we classified as each specific allantoic cell type. Table 4 combines these findings by recording the regional distribution of each cell type.

TABLE 2

Distribution of Incorporated Donor Cells

|  | Mid Region | Distal Region | Fusion Junction | Total |
|---|---|---|---|---|
| n = 10 | 2 (0.04%) | 2794 (51.84%) | 2594 (48.13%) | 5390 |
| Mean ± SEM | 0.2 ± 0.2 | 279.4 ± 181.7 | 259.94 ± 72.0 |  |

TABLE 3

Type of Incorporated Donor Cells

|  | Endothelium | Mesothelium | Mesenchymal | Total |
|---|---|---|---|---|
| n = 10 | 3039 (56.38%) | 433 (8.03%) | 1918 (35.58%) | 5390 |
| Mean ± SEM | 303.9 ± 130.7 | 43.3 ± 22.2 | 191.8 ± 68.7 |  |

TABLE 4

Distribution by Cell Type

|  | Endothelium | Mesothelium | Mesenchymal | Totals |
|---|---|---|---|---|
| Mid Region |  | 2 |  | 2 |
| Distal Region | 1597 | 278 | 949 | 2794 |
| Fusion Junction | 1472 | 153 | 969 | 2594 |
| Totals | 3039 | 431 | 1918 | 5390 |

The above-described experiment showed that: (1) Allantoic cells were able to survive removal from the embryo, overnight culture, dissociation of the cultured allantois, and transplantation into a host embryo. (2) The surviving transplanted cells were able to incorporate into the host embryo. (3) Incorporation occurred primarily in the distal and fusion junction regions of the host allantois. Transplanted cells which adhered to the yolk sac or amnion did not appear to incorporate into these tissues. (4) In the allantois, the transplanted cells appeared as various cell types, including endothelial cells which would be expected to line the vasculature of the umbilical cord. Thus, these transplanted cells could potentially be useful for releasing the products of transfected genes into the bloodstream of a developing fetus. Genetic engineering of these allantoic cells could also be useful for studying the function of various genes in normal vasculogenesis and in malfunctions of vasculogenesis.

II. In Vitro System of Vasculogenesis Materials and Methods i. Mouse strains

Two mouse strains provided embryonic material for this study and were maintained on a 12-hour light/dark cycle (dark period 13.00–1.00). Matings between the F1 generation of (C57BL/6×CBA) provided non-transgenic host conceptuses. F1 females of the (C57BL/6×CBA) strain mated with homozygous lacZ/lacZ males of similar genetic background (ROSA26*, G. Friedrich and P. Soriano, *Genes Dev.* 5:1513–1523, 1991; B. P. Zambrowicz, et al., *Proc. Natl. Acad. Sci. USA* 94:3789–3794, 1997; K. M. Downs and C. Harmann, supra, 1997; K.M. Downs, et al., supra, 1998) provided lacZ-expressing donor allantoises.

ii. Dissection, Staging, and Culture of Conceptuses

Pregnant females were killed by cervical dislocation at 11.00 a.m. on the 8th day of gestation (approximately 7.75 dpc) or the following day at the same time (approximately 8.75 dpc). Conceptuses were dissected from implantation sites (K. M. Downs and R. L. Gardner, *Development* 121:407–416, 1995), Reichert's membrane and associated trophoblast were reflected, and embryos were staged as previously described (K. M. Downs and T. Davies, *Development* 118–1255–1266, 1993) and as described in Brown (N. A. Brown, *Postimplantation Mammalian Embryos: A Practical Approach*, 1990). Normal headfold-stage conceptuses were cultured as previously described by Downs and Gardner (K. M. Downs and R. L. Gardner, supra, 1995) for up to 24 hours if they were to be used for immunohistochemistry or for up to 32 hours if they were to be used as hosts and control conceptuses in transplantation experiments. At the end of incubation, all cultured conceptuses were scored for the extent of morphological development as described in Brown (N. A. Brown, supra, 1990); those showing abnormal development were not used (3.0% were excluded due to stunted growth of the allantois; n=65).

iii. Culture of Allantoises and Dye Exclusion

For survival and vascularization, allantoises were mouth-aspirated into a hand-pulled glass microcapillary (K. M. Downs and R. L. Gardner, supra, 1995; K. M. Downs, et al., supra, 1998) and either cultured in suspension as previously described (K. M. Downs, et al., supra, 1998) or placed individually (i) into wells of 24-well tissue-culture plates (Falcon 3047), (ii) onto glass cover slips (12 mm, Fisher) coated for 30 minutes in filtered (0.45 μm, cellulose acetate) poly-D-lysine (1 mg/ml double processed tissue culture water; Sigma) inserted into wells of 24-well tissue-culture plates and rinsed 34 times with sterile water, (iii) into sterile 8-well plastic chamber slides (Lab-Tek, Nunc), or (iv) into 8-well glass chamber slides some of which were coated in poly-D-lysine. Allantoises were cultured in 0.5 ml (24-well tissue-culture dishes or Falcon culture tubes (K. M. Downs and R. L. Gardner, supra, 1995) or 0.4 ml (8-well chamber slides) of culture medium (Dulbecco's modified Eagle's medium (DMEM) containing either equal parts of immediately-centrifuged and heat-inactivated rat serum as previously described (K. M. Downs and R. L. Gardner, supra, 1995) or 5, 10 and 20% heat-inactivated fetal calf serum (Gibco-BRL; frozen and thawed twice before using) for 24–72 hours at 37° C. in 6.2% $CO_2$ in air. For culture longer than 24 hours, allantoises were given completely fresh medium at 24-hour intervals. In some experiments, erythrosin B (Fisher; 0.04% in phosphate-buffered saline (PBS); H. J. Phillips and J. E. Terryberry, *Exp. Cell Res.* 13:341–347, 1957) was diluted 1:1 in dissection medium to verify allantoic cell viability. Vascular Endothelial Growth Factor (R & D System,s Minneapolis, Minn.) was prepared according to the manufacturer's instructions and was added to culture medium containing 5% FCS in concentrations of 1–20 ng/ml.

DiI (DiI/DiIC18(3); Molecular Probes) labeling of the basal portion of the allantois was carried out in some experiments by dipping the bottom of the allantois into a solution of DiI (1 part 0.5% DiI in absolute alcohol: 9 parts 0.3 M sucrose) as it was held by mouth aspiration in a capillary of slightly smaller diameter. Following culture, DiI-labeled explants were fixed in 4% paraformaldehyde for 1 hour, rinsed in PBS, and examined with fluorescent optics.

At the time of visualization, culture medium was replaced with dissection medium (K. M. Downs and R. L. Gardner, supra, 1995), and the morphology of the allantoises was noted in an inverted compound microscope (Nikon). Some allantoic cultures were fixed in 4% paraformaldehyde at 4° C. for 30 minutes and stained with X-gal (J. R. Sanes, et al., *EMBO J.* 5:3133–3142, 1986) at 37° C. for 12–15 hours.

iv. Dissociation and Transplantation of Cultured Allantoic Cells

For dissociation of plated allantoises, culture medium was removed by suction with a sterile Pasteur pipette, and the allantoises were rinsed once in sterile PBS (dissolved in tissue culture grade distilled water, Sigma). 0.5 ml of trypsin solution (0.05% trypsin, 0.53 mM EDTA, in Hanks' Balanced Salt Solution; Gibco BRL) was added to each well, and the culture plates were incubated at 37° C. in 6.2% $CO_2$ for 10–20 minutes. Trypsin was inactivated by addition of 0.5 ml dissection medium. Allantoic tissue was triturated gently five times with a sterile 5 ml plastic pipette tip (Bio Rad) with the tip opening flamed smooth (I.D. approx. 1 mm). The contents of the wells were combined in a centrifuge tube, and spun in a clinical centrifuge at approximately 1000 revs/minute for 5–10 minutes. After centrifugation, the supernatant was removed and allantoic cells were resuspended in dissection medium.

For each transplanted conceptus, 1 μl of the donor cell suspension, which contained an average of 1042 cells (s.d. 435; n=4 allantoises), was measured onto a sterile tissue culture dish. This drop was mouth-aspirated into a thin hand-pulled glass capillary (I. D. approximately 60 μm), which was then used to inject the donor tissue into a host conceptus that had been cultured overnight and whose own allantois was therefore at a similar stage. The yolk sac of the host conceptus was pierced by the glass capillary in the unvascularized region close to the chorionic membrane to avoid rupturing the yolk sac vasculature and, after piercing the mesothelium of the host allantois, the contents of the capillary were blown out into the interior of the host allantois. Injected host conceptuses were returned to culture for a further 8 hours to allow time for integration of donor cells, after which the fetuses of control and operated host conceptuses contained approximately 14–16-somite pairs. Donor cell contribution to the host was scored as previously described (K. M. Downs and C. Harmann, supra, 1997; K. M. Downs, et al., supra, 1998).

V. Histological Preparation of Conceptuses

Conceptuses were prepared for histological analysis (K. M. Downs and C. Harmann, supra, 1997; K. M. Downs, et al., supra, 1998). Briefly, all conceptuses were fixed in 4% paraformaldehyde for 2 hours at 4° C., and rinsed three times in PBS. If they had been used in transplantation experiments, operated and control conceptuses were then stained with X-gal at 37° C. for 12–15 hours (K. M. Downs and C. Harmann, supra, 1997), but if immunohistochemistry was used on lacZ-containing conceptuses, X-gal-staining was limited to 6 hours. All conceptuses were embedded in paraffin and sectioned at a thickness of either 4 μm or, if they were used for immunohistochemistry, at 6 μm.

vi. Immunohistochemistry

Immunohistochemistry was as previously described (K. M. Downs, et al., supra, 1998), with the exception that immunohistochemistry for VCAM-1 (C-19, Santa Cruz Biotechnology, Inc., cat. # SC-1504) in paraffin-embedded tissue included an unmasking step where, immediately after dewaxing, sections were placed in 10 mM SSC (T. Maniatis, et al., *Molecular Cloning: A Laboratory Manual*, p. 447, 1982), pH 6.0, followed by 1 minute of heating in the microwave to just below the boiling point. This was followed by 1 minute of cooling. Heating and cooling were repeated two times before the SSC was changed, after which the sections underwent five more cycles of heating, cooling and rinsing in SSC. After the last cycle, sections were placed in PBS in preparation for immunohistochemistry. The chromogen diaminobenzidine (DAB; Sigma) was used to detect binding of horseradish peroxidase-conjugated secondary antibodies in single antibody experiments. Experiments involving VCAM-1 initially included Flk-1 controls (Santa Cruz Biotechnology, Inc. cal. #SC-315; K. M. Downs, et al., supra, 1998) and employed embryos older than 6-somite pairs, as these allantoises were previously shown to express VCAM1 (G. C. Gurtner, et al., supra, 1995; L. Kwee, et al., supra, 1995). Once the staining pattern of VCAM-1 was established for older embryos, Flk-l was omitted and older embryos were used in every experiment to compare staining intensity of VCAM-1 in younger allantoises. In experiments involving use of two antibodies or a single antibody in conjunction with X-gal staining, alkaline phosphatase (AP) was conjugated to the secondary antibody and either Fast Blue BB or Fast Red TR salts were used to detect the AP (K. Miller, *Theory and Practice of Histological Techniques*, pp. 435–470, 1996). Control slides were incubated in blocking serum without antibody or in a solution of antibody prebound for 3 hours at room temperature with Flk-1 or VCAM-1 control peptides (Santa Cruz Biotechnology, Inc.; K. M. Downs, et al., supra, 1998). Allantoises that had been cultured on plastic slides and immunostained were coverslipped in aqueous mounting medium (Surgipath, Lerner Laboratories, Pittsburgh, Pa.) and visualized in a compound microscope (Nikon). Some material was counterstained with nuclear fast red or hematoxylin, as described in the figure legends.

vii. Uptake of DiI-Ac-LDL

To distinguish mature endothelial cells from immature endothelial cells, uptake by the allantoic cultures of acetylated low-density lipoprotein labeled with 1,1-dioctadecyl 1,3,3,3,3-tetramethyl-indocarbocyanine perchlorate (DiI-Ac-LDL) was analyzed as described in Dubois, et al. (N. A. Dubois, et al., *Exp. Cell Res.* 196:302–313, 1991). Allantoises cultured for 24 or 72 hours (with feeding), as well as positive control endothelioma (E'oma) cells (J. Obeso, et al., *Lab. Invest.* 63:259–269, 1990) and negative control L929 fibroblasts (American Tissue Culture Collection; generous gifts from Professor Robert Auerbach, University of Wisconsin) were incubated with 10 $\mu$g/ml DiI-Ac-LDL for 12 hours at 37° C. in DMEM containing 5% heat inactivated fetal calf serum or with control medium without DiI-Ac-LDL. The cultures were washed several times with PBS, fixed in 4% paraformaldehyde, and examined with a fluorescence microscope. Fluorescence was visualized using a standard rhodamine excitation/emission filter combination.

viii. Transfection assays

Headfold-stage allantoises were plated individually on 24-well tissue culture plates and cultured for 12 or 18 hours before transfection. At the time of transfection, culture medium was replaced with 0.5 ml heat- and gas-equilibrated DMEM containing 5% fetal calf serum (Gibco-BRL) and allantoises were transfected using a standard $CaHPO_4$ method (F. L. Graham and A. J. van der Eb, supra, 1973) for six hours in 5.0% $CO_2$ at 37° C. by addition of 50 $\mu$l of precipitate containing 1 $\mu$g of pEGFP-NlpEGFP-N1 vector (enhanced Green Fluorescent Protein plasmid, Clontech, Palo Alto, Calif.) driven by the immediate early promoter of human cytomegalovirus. Following incubation, allantoises were washed one time with warm PBS, and returned to incubate at 37° C. in 6.2% $CO_2$ after addition of 0.5 ml heat- and gas-equilibrated culture medium. Expression of enhanced Green Fluorescent Protein was visualized 20–24 hours after the start of transfection using standard epifluorescence microscopy, with a filter set designed for fluorescein detection (488 nm/510 nm).

Results

Survival, Vascularization and Retention of lacZ Expression in Explanted Allantoises We had previously demonstrated that, without exception, all allantoises explanted from whole conceptuses and plated directly onto tissue culture plastic in 24-well plates in DMEM containing an equal volume of rat serum robustly vascularized. To determine the viability and extent of retention of vascular channels in allantoises cultured in these conditions for a longer time period, headfold-stage allantoises were removed from wild-type conceptuses, introduced directly onto the plastic base of culture wells, and observed after 24, 48 and 72 hours. For 48- and 72-hour cultures, allantoises that had been maintained in unchanged culture medium were compared with allantoises that had been given fresh culture medium daily. At these time points, the morphology of the cultured allantoises was noted, and the diameter of the cultures measured. Cell counts were taken at 24 and 72 hours.

Figure 10:
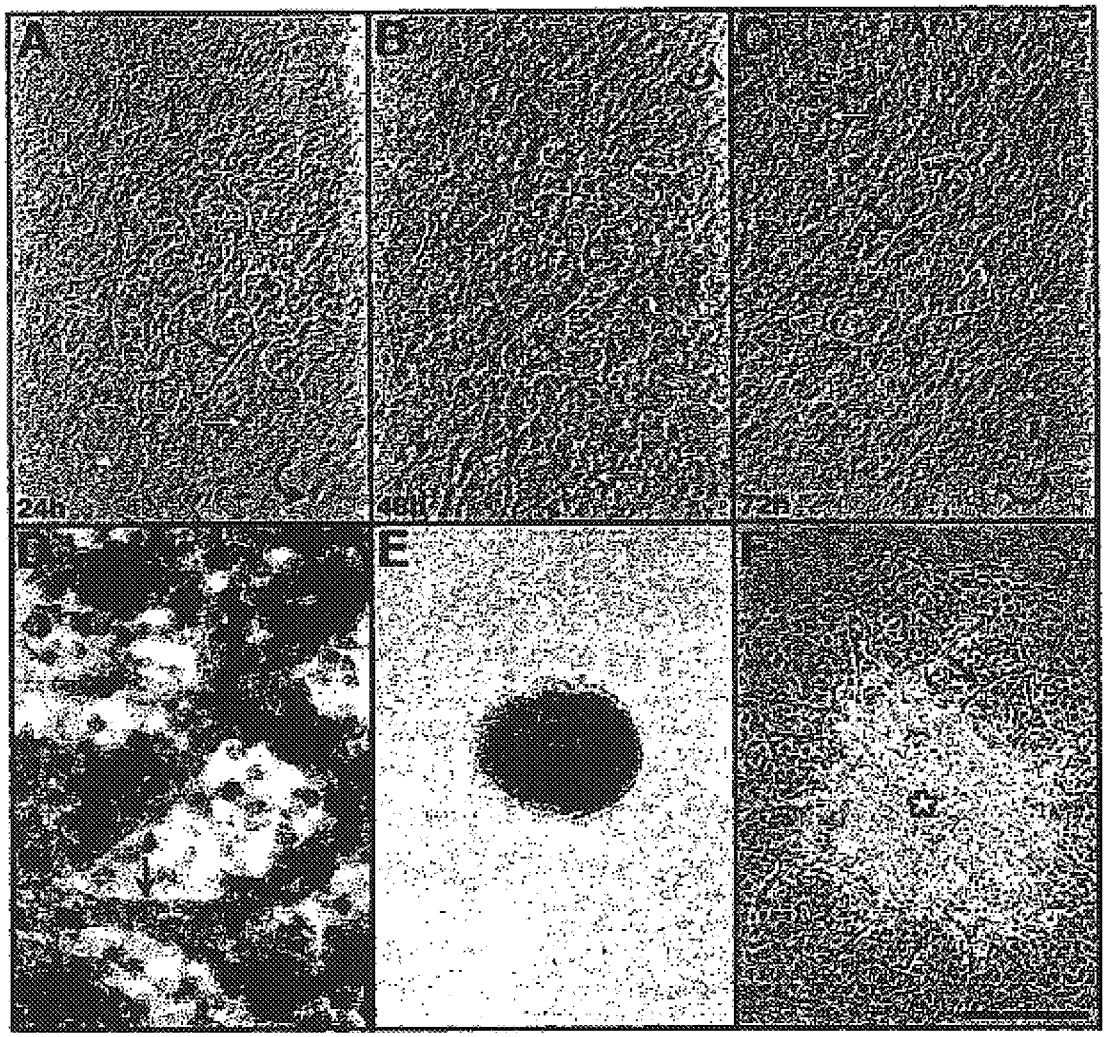
FIG. 10 describes the morphology and lacZ expression in plated headfold-stage allantoises.

FIG. 10 describes the morphology and lacZ expression in plated headfold-stage allantoises. FIGS. 10A–C describe the comparison of a single explanted allantois grown for 24 hours (FIG. 10A), 48 hours (FIG. 10B) and 72 hours (FIG. 10C) in a 24-well tissue culture plate containing an equal volume of rat serum and DMEM. Vascular channels (black arrow, FIGS. 10A–D, F), coalesced clusters of cells (white arrow), and peripheral mesenchymal cells (curved arrow, FIGS. 10A–C, F) are shown. (FIG. 10D): Donor allantoic explant of lacZ/+ genotype cultured for 20 hours and stained in X-gal. All cells were blue. (FIG. 10E): Explanted allantois cultured in 8-well glass chamber slide for 72 hours (and fed at 24 hour intervals) that did not maintain its vasculature (Table 5). (FIG. 10F): Explanted allantois grown for 24 hours in 24-well tissue culture plate in 5% fetal calf serum. Asterisk indicates central mass of undifferentiated cells. Scale bar in 10F: 300 $\mu$m (10A–C); 72 $\mu$m (10D); 240 $\mu$m (10E); 310 $\mu$m (10F).

At 24 hours, all plated allantoises had flattened out on the bottom of the dish and spread to form a circular mass of closely packed cells. They did not fill the bottom of the culture well. All allantoises underwent vasculogenesis as evidenced by the development of conspicuous vascular networks, appearing as complex, criss-crossing channels throughout all but the peripheral-most region of the allantois (K. M. Downs, et al., 1998; FIG. 10A; Table 5).

Figure 11:
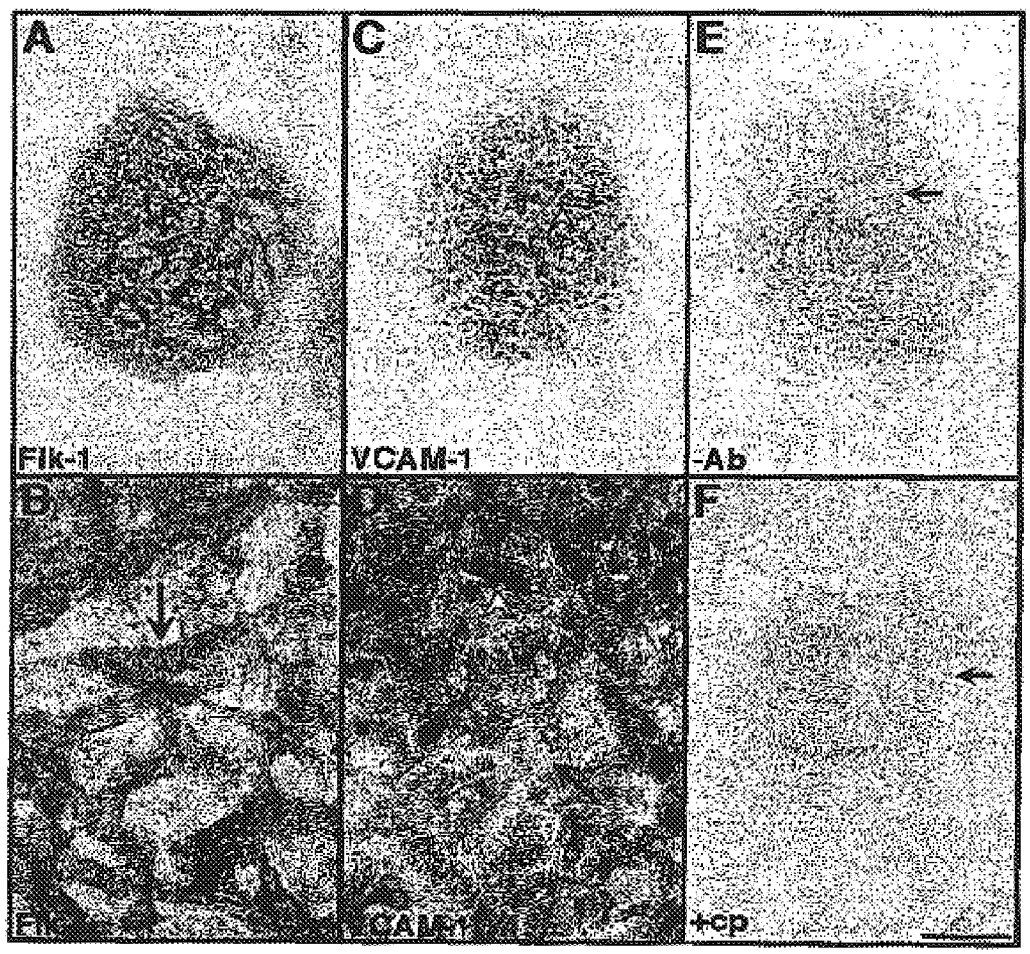
FIG. 11 describes the immunohistochemistry used to localize Flk-1 and VCAM-1 in plated headfold-stage allantoises.

Coalesced clusters of cells were observed in association with vascular channels, and flattened cells were found in all spaces between the vascular channels. Spindle-shaped fibroblast-like cells adherent to the plastic were visible at the perimeter of the circular allantoic mass. The vascular plexus and coalesced clusters expressed flk-1 whereas the fibroblast-like cells on the periphery did not (K. M. Downs, et al., 1998; FIGS. 11A, B). FIG. 11 describes the immunohistochemistry used to localize Flk-1 and VCAM-1 in plated headfold-stage allantoises. Allantoises were explanted and plated individually in 8-well plastic chamber slides containing an equal volume of rat serum and DMEM and cultured for 24 hours. Vascularized explants were prepared for immunohistochemistry as described in Materials and Methods. (FIGS. 11A, B): Low and high magnification of anti-Flk-1-stained (brown) allantoises. (FIGS. 11C, D): Low and high magnification of anti-VCAM-1-stained (brown) allantoises. (FIGS. 11E, F): Control allantoises minus primary antibody (FIG. 11E) and primary antibody prebound with control peptide (FIG. 11F). Tissue in all panels was counterstained with hematoxylin. Scale bar in (FIG. 11F): 230 μm (FIGS. 11A, C, E, F); 58 μm (FIGS. 11B, D).

The majority, if not all, of the flattened cells in between the vascular plexus also appeared negative for Flk-1 (K. M. Downs, et al., 1998; FIG. 11A, B). Counting at the end of 24 hours revealed an average of 5101 cells per allantois (3 experiments, n=29 allantoises).

(18.2%) or no (63.6%) vasculature (n=11 unfed allantoises). In the latter, much of the culture now consisted of fibroblast-like cells, with greater distances between cells on the periphery.

Allantoises removed from lacZ/+ transgenic conceptuses and cultured as described above, retained X-gal activity throughout the entire culture period (FIG. 10D). However, as outlying cells were isolated from other cells and spread out more thinly on the plate, they were easily overfixed, which blocked X-gal staining (K. M. Downs and C. Harmann, supra, 1997). Fixation times of 10 or 30 minutes allowed blue staining throughout the cultures, including the outlying cells, whereas 90 minutes of fixation blocked staining only in the latter.

Survival and Vascularization of Explanted Allantoises in Different Culture Conditions

| Condition | Substratum | Culture Medium (volume) | No. Expts | No. Plated | No. Survived | Vascularization | | |
|---|---|---|---|---|---|---|---|---|
| | | | | | | 24 hours | 48 hours | 72 hours |
| 1 | Falcon plastic | 50% rat serum (0.5 ml) | 10 | 35 | 35 (100.0%) | Throughout (100.0%) | Throughout (100.0%) | Throughout (94.3%) |
| 2 | poly-D-lysine coated glass cover slips | 50% rat serum (0.5 ml) | 3 | 16 | 16 (100.0%) | Throughout (81.2%) | Throughout (100.0%) | Throughout (100.0%) |
| 3* | poly-D-lysine-coated glass slides | 50% rat serum (0.4 ml) | 3 | 12 | 12 (100.0%) | Throughout (83.3%) | Throughout (75.0%) | Throughout (50.0%) |
| 4* | 8-well glass slides | 50% rat serum (0.4 ml) | 3 | 10 | 10 (100.0%) | Throughout (60.0%) | Throughout (50.0%) | Throughout (10.0%) |
| 5* | 8-well plastic slides | 50% rat serum (0.4 ml) | 3 | 10 | 10 (100.0%) | Throughout (90.0%) | Throughout (50.0%) | Throughout (30.0%) |
| 6 | Falcon plastic | 5% FCS (0.5 ml) | 6 | 20 | 19 (95.0%) | Periphery† (100.0%) | None†† (0.0%) | None†† (0.0%) |
| 7 | Falcon plastic | 10% FCS (0.5 ml) | 3 | 7 | 7 (100.0%) | Throughout (100.0%) | Breaking Down (71.4%) None†† (28.6%) | None†† (0.0%) |
| 8 | Falcon plastic | 20% FCS (0.5 ml) | 3 | 8 | 8 (100.0%) | Throughout (100.0%) | Throughout (87.5%) Breaking Down (12.5%) | Throughout (12.5%) Breaking Down (62.5%) None†† (25.0%) |

Table 5. Comparison of vscularization of headfold-stage allantoises under different culture conditions. Allantoises were explanted and cultured (with feeding at 24-hour intervals) in DMEM-based media as described in the Table for 24–72 hours. All experiments included controls plated in 24-well dishes of Falcon plastic containing equal volumes of heat-inactivated rat serum and DMEM. The shaded rows indicated conditions most favorable to vascularization of explants.
*Allantoises that had not vascularized rounded up into plastic-adherent balls.
†The vasculature of average- to large-volume allantoises emanated from a central clump of undifferentiated cells (FIG. 1E), whereas vascularization in smaller explants occurred throughout, with no residue of undifferentiated cells in the explant's center.
††Adherent fibroblast-like cells only were observed.

By 48 hours, cultures that had been fed fresh medium at 24 hours had physically enlarged and reorganized (Table 5; compare FIG. 10A and B). In addition, cells on the periphery had spread and were no longer confluent with each other. In the absence of feeding, vascular channels had begun to break down (data not shown) and there was a trend toward smaller diameter in comparison with fed ones.

Feeding cultures at 48 hours resulted in significantly larger allantoises by 72 hours (data not shown), with an average number of 9129 cells per allantois (3 experiments, n=13 allantoises). The vasculature was intact and robust in the majority of explants (Table 5) though its appearance had again changed (compare FIG. 10B and C). Vascular channels were less extensive and the remaining vascular lumina were generally wider than observed at the previous two timepoints (compare FIG. 10A–C). Fed cultures maintained flk-1 expression in the vascular channels at levels similar to those observed after 24 hours (data not shown). 18.2% of the unfed cultures retained vasculature, but others showed little To determine whether the foregoing culture conditions were optimal for survival and differentiation of allantoic explants, we investigated growth and vascularization of explanted headfold-stage allantoises under several different conditions. In addition to tissue culture plastic, allantoises grew and vascularized for up to three days on poly-D-lysine coated glass cover slips (Table 5). However, allantoises fared less well in other conditions (Table 5). Although many allantoises initially vascularized in 8-well chamber slides, vascularization was not maintained over the 72-hour time period (Table 5). Where vascularity had been lost in cultures in chamber slides, allantoises rounded up into adherent balls (FIG. 10E).

Cell numbers at the end of the 24-hour culture period in explants grown in 5% FCS were slightly lower than those of allantoises grown in rat serum (4417 cells per allantois, 3 experiments, n=12 allantoises); further, their gross morphological appearance was somewhat different (FIG. 10F). First, the flattened cells at the periphery of the allantoic mass presented a well-circumscribed, rather than diffuse, border. Second, in those allantoises that were initially of average or large volume, a Flk-1-positive vascular plexus had formed, but rather than criss-cross throughout the allantois, it emanated from a central core of morphologically undifferentiated cells (FIG. 10F). Immunostaining revealed the presence of flk-1- and VCAM-1-expressing cells (data not shown), suggesting that the core comprised angioblasts and mesothelial cells.

Despite feeding, allantoises cultured in 5% FCS were typically devoid of vascular channels by 48 hours. By 72 hours, explants fed medium containing 5% FCS at 24-hour intervals contained an average number of 5649 cells per allantois in two experiments (N=5), and consisted predominantly of mesenchymal cells. Increasing the concentration of FCS to 10–20% FCS resulted in partial maintenance of vascular channels for up to 72 hours in only 12.5% of the explants. Finally, although explants cultured in 10% rat serum were indistinguishable from those cultured in 5% FCS, increasing the rat serum to 20% resulted in explants indistinguishable from those cultured in 50% rat serum (data not shown).

Thus, a high concentration of some factor(s) must be required for both formation and maintenance of endothelial cells in allantoic explants, either directly or through maintenance of the mesothelium, previously hypothesized to play a role in vascularization of the core mesoderm (K. M. Downs, et al., supra, 1998). To test that possibility, recombinant VEGF (1–10 ng/ml culture medium) was added to explants at the start of culture in 5% FCS. Feeding at 24 hour intervals in the presence of VEGF (2–10 ng/ml) resulted in retention of Flk-1 containing vascular channels and overlying VCAM-1 positive cells by 72 hours whereas untreated explants or those treated with 1 ng/ml of VEGF were devoid of such channels. Further cell survival was enhanced (78% relative to the controls 36% in FCS alone).

Together these findings suggest that varying the culture conditions of allantoic explants through serum starvation or enrichment varies the state of the endothelial cells, with low serum favoring formation of non-epithelialized angioblasts, and high serum favoring formation of endothelial channels. At least one of the key growth factors required in formation and maintenance of the vascularity appears to be VEGF. In addition, there appears to be a strong correlation between co-retention of endothelial and mesothelial cells.

Time Course of Allantoic Vasculogenesis in Explant Cultures

Figure 12:
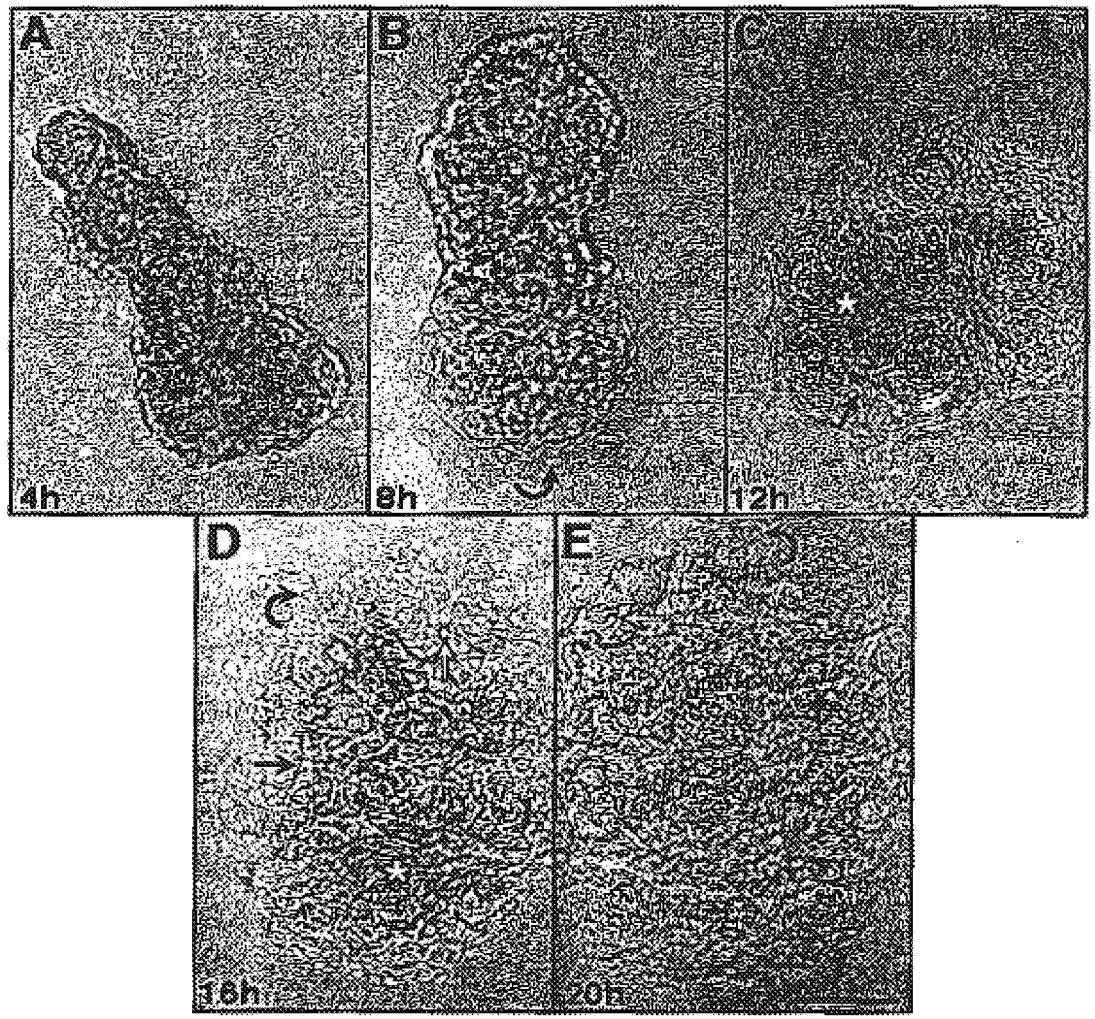
FIG. 12 illustrates the time course of vascularization in plated headfold-stage allantoises.

To discover whether headfold-stage allantoises vascularized stereotypically in vitro, allantoises were plated individually in 24-well tissue-culture dishes, cultured in DMEM containing rat serum (1:1), and observed at 4-hour intervals for up to 24 hours (FIG. 12). At 4 hours after lating, allantoises had attached to the plastic, but were little changed from their initial morphology, appearing just slightly larger and flattened but still retaining their elongated and tapered shape (FIG. 12A). At 8 hours, a small number of allantoises resembled those at 4 hours, but most were well-attached to the tissue culture plastic and exhibited fibroblast-like cells spreading out from the allantois (FIG. 12B). By 12 hours, all allantoises were well-adhered to the plastic and most were still somewhat elongated. At one end of the allantoic projection, cells were beginning to vascularize whereas at the opposite end, cells were piled up and appeared morphologically undifferentiated as described above (FIG. 12C). Labeling the basal end with DiI prior to plating confirmed that the latter was the base of the allantois (data not shown).

At 16 hours, all allantoises were well-vascularized, with criss-crossing vascular channels almost fully obscuring the few cells still piled up at the basal end of the allantois (FIG. 12D). Allantoises cultured for 20 hours (FIG. 12E) were indistinguishable from those at 24 hours (compare FIGS. 12E and 10A; also, K. M. Downs, et al., supra, 1998). The flattened allantoic mass was nearly perfectly round by this time and contained a regular criss-crossing vascular plexus in all but the peripheral-most regions, which was populated by a single layer of mesenchymal cells. DiI labeling revealed that cells from the basal region became incorporated into the vasculature, as well as into the overlying mesenchymal and attached mesothelial cell populations (date not shown). Thus, allantoises in isolation culture appear to differentiate stereotypically, and maintain the distoproximal gradient of differentiation (K. M. Downs and C. Harmann, supra, 1997; K. M. Downs, et al., supra, 1998).

Transplantation of Cultured Donor lacZ/+ Allantoic Cells into Host Conceptuses

Transplantation was used to determine whether allantoic cells cultured for 24 hours were able to appropriately colonize host allantoises. Following dissociation, a portion of the donor cells was counted, some were replated to ensure viability and retention of lacZ-expression following dissociation, and others were transplanted into the allantoises of host conceptuses.

A total of 30 headfold-stage host conceptuses was cultured for 24 hours in three experiments. Two of 30 hosts were discarded, as they contained allantoises that had not fused with the chorion by the end of the culture period and were therefore judged abnormal. In the remaining 28 conceptuses, the yolk sac in the unvascularized region close to the chorion was pierced with a glass capillary containing donor cells (FIG. 13A) which was then directed into the host allantois (FIG. 13B) and the donor cells were gently blown in. Injected host conceptuses were returned to culture for 8 hours to allow time for integration of donor cells, after which all 28 operated host conceptuses (FIG. 13C) were judged chimeric following X-gal staining (range of incorporated cell fragments 5-2239).

Figure 13:
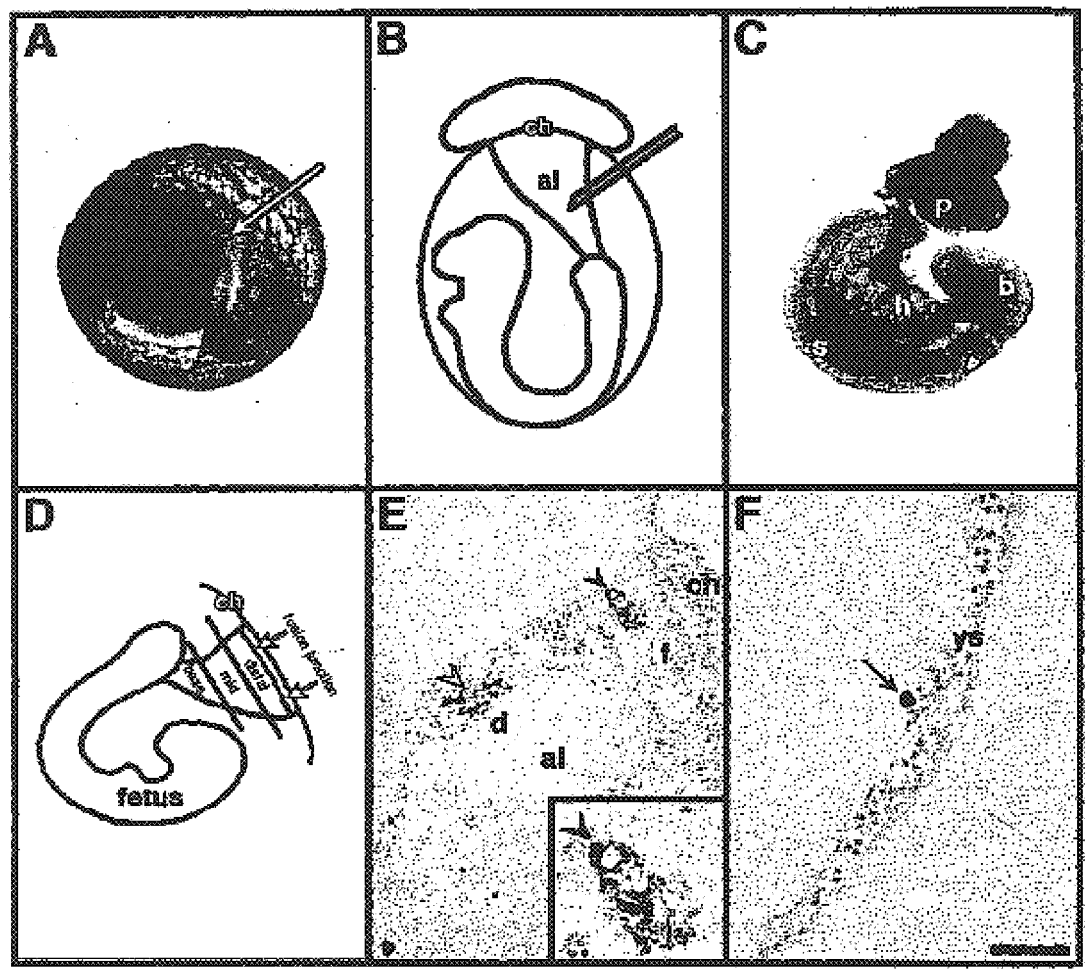
FIG. 13 describes transplantation of cultured donor lacZ/+ allantoic cells into cultured host conceptuses.

All injections resulted in donor cell integration into host allantoises. Colonization of donor allantoic cells was confined to the distal region and fusion junction of the host's allantois (FIG. 13D, E) and occurred with similar frequencies (data not shown). FIG. 13 describes transplantation of cultured donor lacZ/+ allantoic cells into cultured host conceptuses. (FIG. 13A): 8.75 dpc cultured benzidine-stained (K. M. Downs and C. Harmann, supra, 1997) host conceptus viewed from the region of the ectoplacental cone to show the vessel-free region in the yolk sac (white arrow) selected for injection of donor cells into the allantois. (FIG. 13B): Schematic diagram of cultured 8.75 dpc conceptus in sagittal orientation showing the distal site of injection of donor cells into the host allantois. (FIG. 13C): Operated 8.75 dpc host conceptus cultured for a further 8 hours, viewed following removal of its yolk sac. (FIG. 13D): Schematic diagram of the fetus in FIG. 13C showing the regions of the allantois used to score the location of blue donor cells. (FIG. 13E): Cultured lacZ/+ blue donor cells are visible in the distal (d, white arrowhead) and fusion junction (f, black arrowhead) regions of the host allantois. Insert: A higher magnification view of donor cells in the chorioallantoic fusion junction shows incorporation of donor cells in the host endothelium. (FIG. 13F): A clump of unincorporated donor cells (arrow) in contact with, but not integrated into, the host yolk sac. Conceptuses in (13E, F) were counterstained in Nuclear Fast Red. Referring to FIG. 13, abbreviations are: al, allantois; b, brain; ch, chorion; h, heart; p, placenta; s, somites; ys, yolk sac. Scale bar in (FIG. 13F): 700 μm (FIGS. 13A, C); 200 μm (FIG. 13E); 70 μm (FIG. 13E, insert); 50 μm (FIG. 13F).

Figure 14:
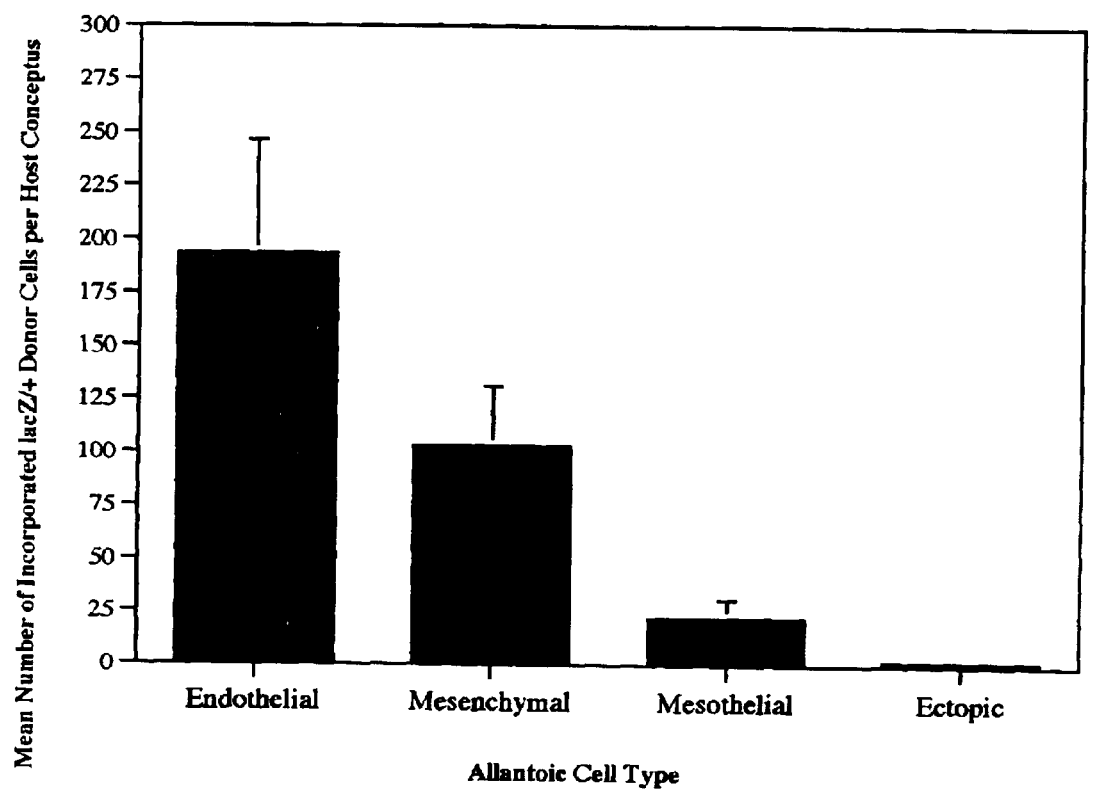
FIG. 14 plots the average number of donor lacZ/+ allantoic cells incorporated into host allantoises according to cell type.

FIG. 14 plots the average number of donor lacZ/+ allantoic cells incorporated into host allantoises according to cell type. Mean number of donor cell fragments that incorporated into the host allantois were classified as endothelial, mesothelial or mesenchymal cells. Donor cells that had integrated ectopically (yolk sac or amnion) are also indicated.

The incorporated cells appeared as three types (FIG. 14): the majority were endothelial, the fewest representatives were found in the mesothelium, and others were solitary mesenchymal-like cells, not part of the endothelium or mesothelium. A few ectopically incorporated cells were found in the yolk sac and amnion and were limited to the mesothelial cell layer (FIG. 14). Donor cells were never found integrated in the fetus. A very small number of allantoic red blood cells was blue but, as reported previously, these were assumed to be host erythroid cells that had become associated with donor endothelium (K.M. Downs, et al., supra, 1998).

The average number of incorporated cells over three experiments was 31% of the total estimated number of cells that had been injected. 34% of injected cells were found as unintegrated clumps within the host conceptuses. Of these, approximately half were located within the allantois. The others were located either (i) free in the exocoelomic cavity, (ii) associated with but not adherent to the yolk sac or amnion in the exocoelom (FIG. 13F), (iii) within the ectoplacental cone, or (iv) within the lumen of the gut. In the last category, donor cells had likely become adherent to the outer surface of the conceptus during injection and were internalized as the gut formed. Based on these calculations, we conclude that the remaining 35% of injected cells were likely lost to the dissection medium during transplantation.

As a prelude to determining the Flk-1 status of donor cells in chimeric hosts, flk-1 expression was compared in freshly-recovered conceptuses (approximately 12-somite pairs) and headfold-stage conceptuses cultured to at least 12-somite pairs. We had previously reported that allantoic maturity, i.e., competence of the allantois to fuse with the chorion, appears to be under the control of an internal timing mechanism which correlates with the number of somite pairs contained in the fetus (K. M. Downs and R. L. Gardner, supra, 1995; reviewed in K. M. Downs, supra, 1998). Headfold-stage embryos cultured for 23–24-hours contain an average of 12-somite pairs at the culture endpoint (K. M. Downs and C. Harmann, supra, 1997; K. M. Downs, et al., supra, 1998); thus, headfold-stage allantoises cultured for 24 hours are considered to be the equivalent of intact allantoises of hosts containing approximately 12-somite pairs.

Figure 15:
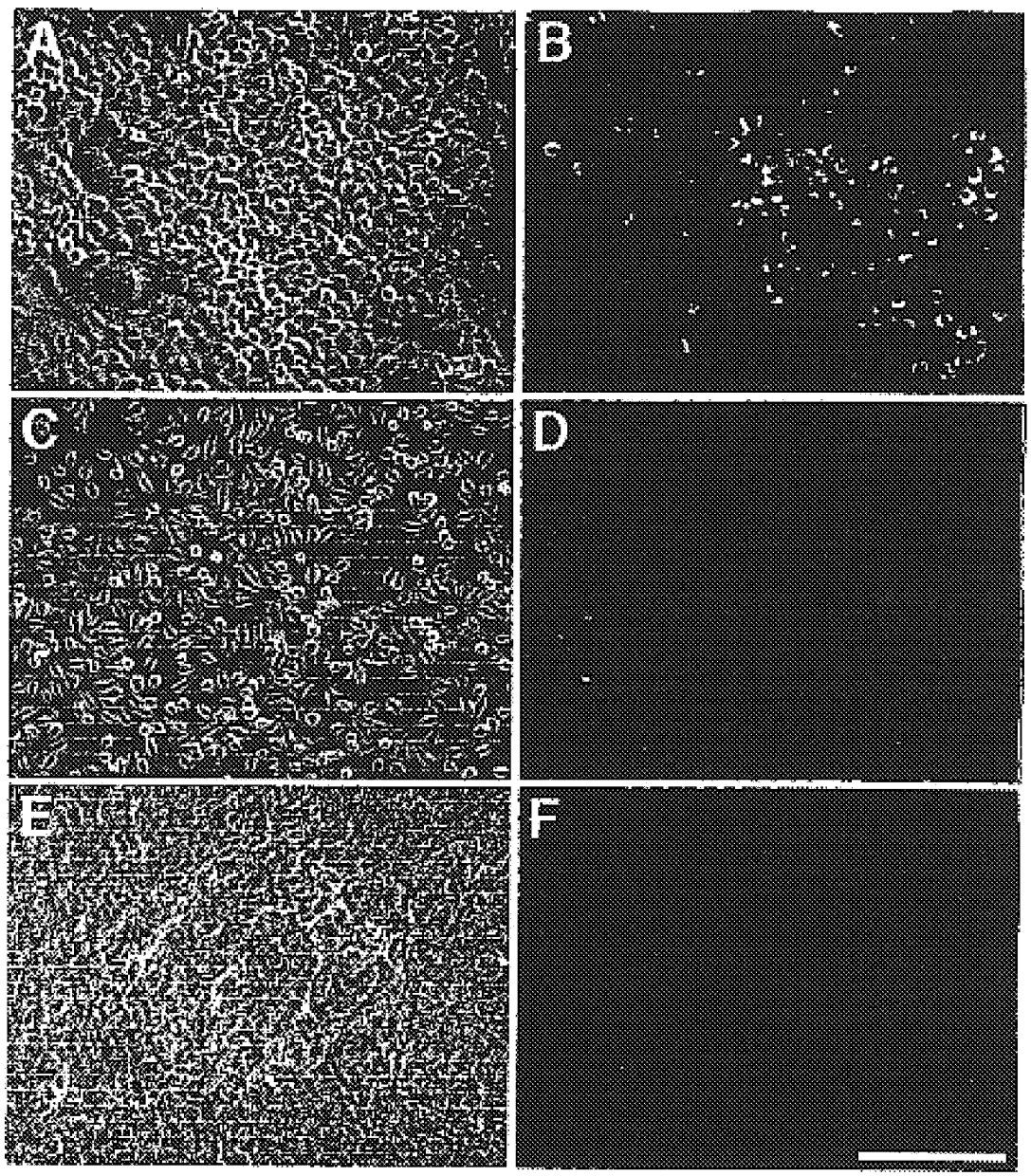
FIG. 15 illustrates localization of Flk-1 in allantoises of freshly-recovered (FIG. 15A), cultured (FIG. 15B) and cultured chimeric (FIG. 15C) conceptuses.

FIG. 15 illustrates localization of Flk-1 in allantoises of freshly-recovered, cultured and cultured chimeric conceptuses. Allantois from (FIG. 15A) a freshly-recovered 8.75 dpc conceptus (approximately 14–16-somite pairs) and (FIG. 15B) a headfold-stage conceptus cultured for 24 hours (approximately 14–16 somite pairs) show flk-1 expression (brown staining) in the nascent vasculature (closed arrows). (FIG. 15C): Chimeric host conceptus containing integrated cultured lacZ/+ donor cells at the chorio-allantoic fusion junction. Black arrowheads indicate those blue donor lacZ/+ cells as a result of reaction with X-gal that contain Flk-1, red as a result of reaction with alkaline phosphatase/Fast Red TR salt. White arrow indicates donor cells that are integrated in the mesothelium (and Flk-1) or clumped. (FIG. 15D): Higher magnification view of doubly-stained X-gal/Flk-1-positive donor cells (black arrowheads). White arrow as in (FIG. 15C). Conceptuses in FIGS. 15A and B were counterstained in hematoxylin. Abbreviations as in FIG. 13. Controls for X-gal staining were as previously described (K. M. Downs and C. Harmann, supra, 1997); controls for Flk-1 in both cultured and ex vivo control conceptuses for all panels were as previously described (K. M. Downs, et al., supra, 1998). Scale bar in (FIG. 15D): 53 μm (FIGS. 15A, B and C); 12 μm (FIG. 15D).

In both ex vivo and cultured conceptuses, Flk-1 was localized to the allantoic vasculature and was not expressed in mesothelium (FIGS. 15A, B). In operated chimeric hosts, many, but not all, donor cells that had incorporated into the host's allantoic vasculature exhibited Flk-1 (FIGS. 15C, D). None of the donor cells that had integrated into the mesothelium contained Flk-1, whereas clumps of unincorporated cells contained both Flk-1-positive and Flk-1-negative cells.

DiI-Ac-LDL Uptake

The ability of cultured allantoic cells to take up DiI-Ac-LDL was examined to obtain further evidence that the Flk-1-positive cells were endothelial, with the caveat, however, that many (J. F. Nagelkerke, et al., J. Biol. Chem. 258:12221–12227, 1983; Voyta, et al., 1984; J. D. Rone and A. L. Goodman, supra, 1987; Z. Yablonka-Reuveni, Dev. Biol. 132:230–240, 1989; N. Chung-Welch, et al., Differentiation 42:44–53, 1989; N. A. Dubois, et al., supra, 1991; T. Sakamoto, et al., Curr. Eye Res. 14:621–627, 1995), but not all (J. D. Rone and A. L. Goodman, supra, 1987; J. Plendl, et al., Anat. Embryol. 194:445–456, 1996), endothelial cells take up DiI-Ac-LDL.

Figure 16:
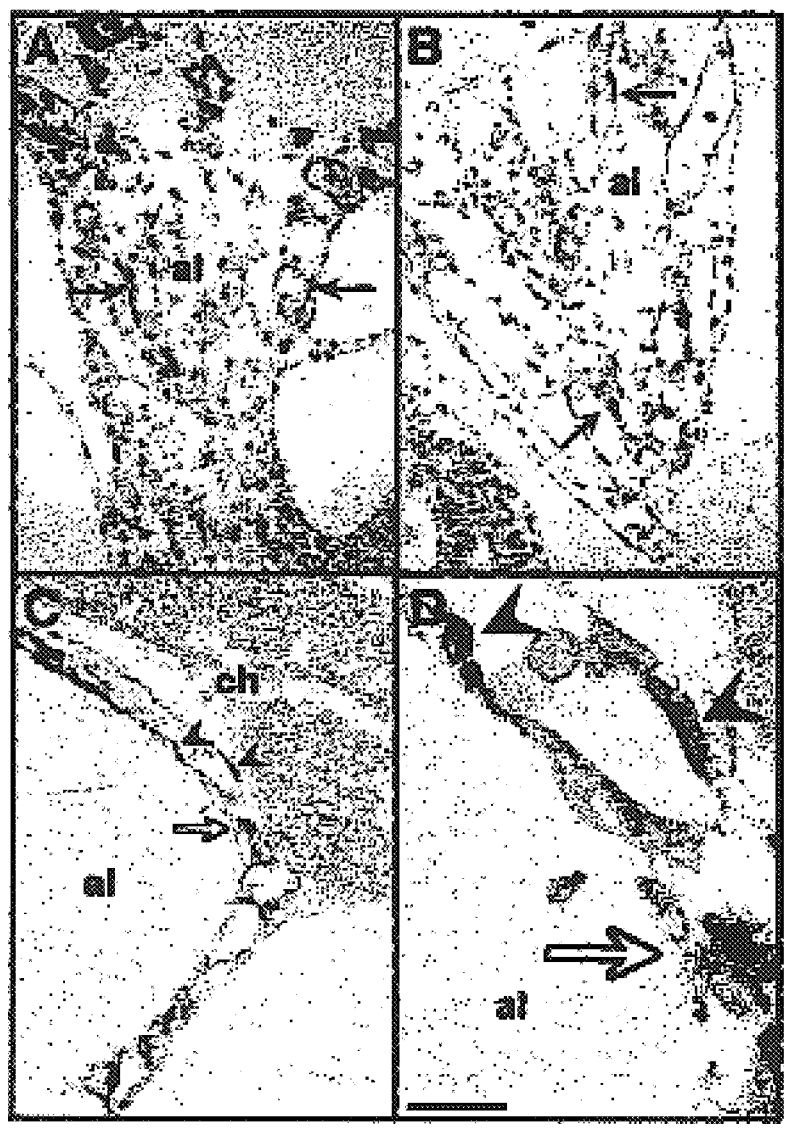
FIG. 16 is a set of light—(FIGS. 16A, C, E) and fluorescent—(FIGS. 16B, D, F) micrographs of E'oma cells (FIGS. 16A, B), L929 fibroblasts (FIGS. 16C, D) and headfold-stage allantois plated for 72 hours (FIGS. 16E, F).

FIG. 16 illustrates uptake of DiI-Ac LDL. Light-(FIGS. 16A, C and E) and fluorescent- (FIGS. 16B, D and F) micrographs of E'oma cells (FIGS. 16A and B), L929 fibroblasts (FIGS. 16C and D) and headfold-stage allantois plated for 72 hours (FIGS. 16E and F), all exposed to acetylated-DiI-low density lipoprotein for 12 hours as described in Materials and Methods.

Allantoises cultured for 24 and 72 hours (3 experiments per time point, ≧2 allantoises per experiment), as well as positive (E'oma) and negative (L929) control cell lines, were exposed to DiI-Ac-LDL for 12 hours. After removal of the excess DiI-Ac-LDL, cultures were examined for fluorescence. As expected, the control E'oma cells did show uptake of the fluorescent label (FIGS. 16A and B), whereas L929 fibroblasts did not (FIGS. 16C and D). All allantoic cultures treated in the presence of DiI-Ac-LDL showed no fluorescent labeling, either in the vascular channels or in the surrounding cells (FIGS. 16E and F).

Expression of VCAM1 in Intact and Explanted Allantoises

VCAM-1 is required in mesothelium for fusion of the allantois with the chorion (G. C. Gurtner, et al., supra, 1995; L. Kwee, et al., supra, 1995; J. T. Yang, et al., supra, 1995) and it is the only gene whose protein product has thus far been clearly demonstrated in allantoic mesothelium. As a prelude to investigating the presence and whereabouts of mesothelium in cultures of explanted allantoises, spatiotemporal expression patterns of VCAM1 were analyzed in whole ex viva conceptuses (headfold-to-8-somite pair stages).

Figure 17:
FIG. 17 describes the spatiotemporal appearance of VCAM-1 in freshly-recovered conceptuses.

FIG. 17 describes the spatiotemporal appearance of VCAM-1 in freshly-recovered conceptuses. Freshly-recovered conceptuses prepared for immunostaining against VCAM-1. (FIG. 17A): Allantois at late headfold-stage (LHF) showing one VCAM-1-positive cell (brown) in the putative mesothelium (white arrowhead). Black arrowheads indicate mouse hairs in cross-section inserted as fiducial markers for experiments not described in this application. (FIG. 17B): Allantois at 4-somite pairs (4-s) showing VCAM-1-positive mesothelium (white arrowhead) and VCAM-1-positive core cells (white arrow). (FIG. 17C) 6-somite pair (6-s) allantois. (FIG. 17D) 8-somite pair (8-s) allantois. Arrowheads and arrows as in (FIG. 17B). (FIG. 17E) 8-somite pair control conceptus without antibody (−Ab). (FIG. 17F) 8-somite pair control allantois in which antibody to VCAM-1 was prebound with control VCAM-1 peptide (+cp). All conceptuses were counterstained in hematoxylin. Abbreviations as in FIG. 12; am, amnion; ps, region of the primitive streak. Scale bar in (FIG. 17F): 40 μm (FIG. 17A); 78 μm (FIG. 17B); 110 μm (FIG. 17C); 120 μm (FIGS. 17D, E and F).

VCAM-1 was not detected in late neural plate stage allantoises. At headfold stages, up to half of the distal allantois contained a flattened exterior layer of putative mesothelial cells (K. M. Downs, et al., supra, 1998) but expression of VCAM1 was found in just a few outer distal cells in a small number (33.3%) of allantoises (FIG. 17A). However, between 2- and 8-somite pairs, VCAM1 expression spread proximally in the mesothelium of all allantoises (FIGS. 17B–F). Initially, levels of VCAM-1 were modest but increased with allantoic age, the most lightly staining cells always the most proximal. By 6–8-somite pairs, levels of VCAM-1 were highest throughout all but the mesothelium in the basal region, which appeared negative in all allantoises at all developmental stages (FIGS. 17C–F). Some individual mesothelial cells within largely VCAM-1-positive tracts were lightly stained or negative at all developmental stages examined.

In addition to mesothelium, VCAM-1 was found in core allantoic mesoderm. Expression in the core was, however, delayed with respect to the overlying mesothelium, first being detectable at 3–4 somite pairs (FIG. 17B). At these and all stages examined thereafter, levels of VCAM-l in the core were similar to those found in the immediately suprajacent mesothelium and extended only as far as the VCAM-1-positive mesothelium extended proximally (FIGS. 17B–D).

Figure 18:
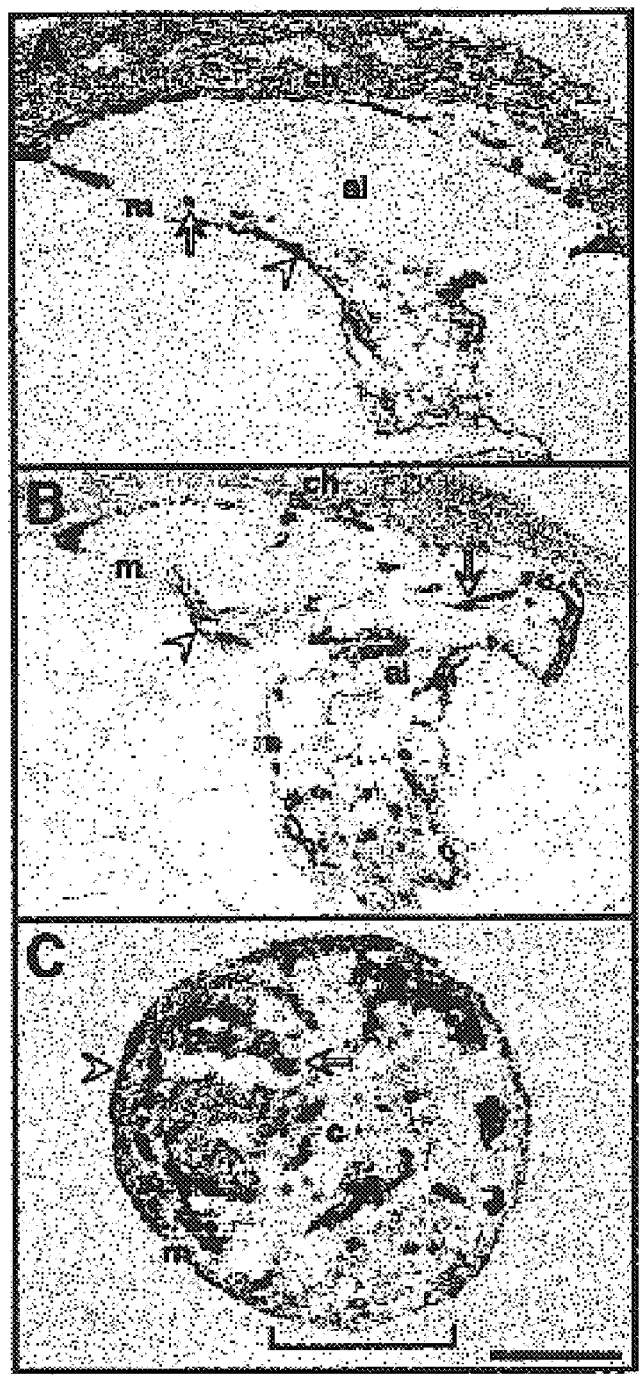
FIG. 18 illustrates simultaneous localization of Flk-1 and VCAM-1 in intact and suspended allantoises.

FIG. 18 illustrates simultaneous localization of Flk-1 and VCAM-1 in intact and suspended allantoises. Freshly recovered conceptus containing 14-somite pairs (FIG. 18A) and headfold-stage conceptus cultured to 14-somite pairs (FIG. 18B) were prepared for immunohistochemistry as described above and immunostained with antibodies against Flk-1 (blue) and VCAM-1 (brown). White arrowheads, VCAM-1-positive mesothelium; white arrows, VCAM-1-positive core allantoic cells associated with the Flk-1-positive vascular plexus. (FIG. 18C): Explanted headfold stage allantois cultured in suspension for 24 hours and doubly-immunostained as described in (FIGS. 18A and B). The proximal region is indicated by the horizontal bar beneath the explant. m, mesothelium; c, core allantoic cells. Scale bar in (FIG. 18C): 160 μm (FIGS. 18A and B); 88 μm (FIG. 18C).

Double immunohistochemistry with Flk-1 revealed that VCAM-1-positive core cells were associated with but exclusive of the Flk-1-positive vasculature in both freshly-recovered and cultured conceptuses (12–16 somite pairs; FIGS. 18A, B). VCAM-1-positive core cells were never associated with the vasculature at the base of the allantois (FIGS. 17, 18). In addition, cells that contained neither Flk-1 nor VCAM-1 were scattered throughout allantoises.

We next looked for the presence of mesothelium in explanted allantoises and determined its topographical relationship to the allantoic vasculature by immunostaining with antibodies against VCAM-1 and comparing this staining pattern with that of Flk-1 (FIG. 11). By altering the focal plane during light microscopy, we found that VCAM-1-positive cells were distributed on top of the vascular plexus in explanted allantoises (FIGS. 11C–F). The peripheral fibroblast-like cells appeared negative for VCAM-1 (FIG. 11C) as they were for Flk-1 (FIG. 11A). Thus, allantoic mesothelium was present in culture in close association with the vasculature.

To provide further evidence that mesothelium survived culture, allantoises were suspended and cultured, rather than plated. We had previously shown that, in suspension, allantoises round up, and consist of an inner core of mesoderm encapsulated by a rind of putative mesothelium (K. M. Downs, et al., supra, 1998). Here, double immunohistochemistry with antibodies against both VCAM-1 and Flk-1 was applied to suspended allantoises. We found that the outer rind of these was strongly VCAM-1-positive (FIG. 18C). Intriguingly, a short continuous tract of rind was VCAM-1-negative, which we interpreted as equivalent to the negative basal region of intact allantoises (FIGS. 17C, D and 18A, B). A hair placed in the base of the allantois prior to culture and immunostaining provided support for this interpretation, as all cells in the region of the hair were VCAM-1-negative. In addition, VCAM-1-positive core cells were found in association with the Flk-1 vasculature at the presumptive distal pole of suspended allantoises (FIG. 18C). Together, these results provided further support that mesothelium was present in culture in close juxtaposition to the vasculature.

Transfection of Plated Allantoises Before and After Vascularization

On the basis of gene expression in intact allantoises and morphology, we conclude that at least three major cell populations are present in explanted allantoises: Flk-1-positive endothelial cells of the vasculature, VCAM-1-positive mesothelial cells overlying the vasculature, and a peripheral population of flattened mesenchymal cells that express neither flk-1 nor VCAM1. Downs, et al. have recently proposed that allantoic cells might be an attractive vehicle for the delivery of therapeutic factors to the fetal blood circulation in order to ameliorate certain developmental defects. Thus, to determine whether any of the three allantoic cell types could take up and express exogenous DNA, allantoises were transfected via the calcium phosphate precipitate method (F. L. Graham and A. J. van der Eb, supra, 1973) with a plasmid containing enhanced GFP expressed from the human cytomegalovirus early promoter.

Allantoic explants that had been cultured for 12 and 18 hours were exposed to the DNA precipitate for 6 hours. Shorter exposure times of 1, 2 and 4 hours resulted in healthy cultures but fewer transfectants, and an exposure time of 8 hours resulted in optimal numbers of transfectants but more dead cells (data not shown). Immediately after transfection, fresh DMEM-containing rat serum replaced 5% fetal calf serum and was also fed to the absolute controls, and all cultures were returned to the incubator for a further 20–24 hours.

Figure 19:
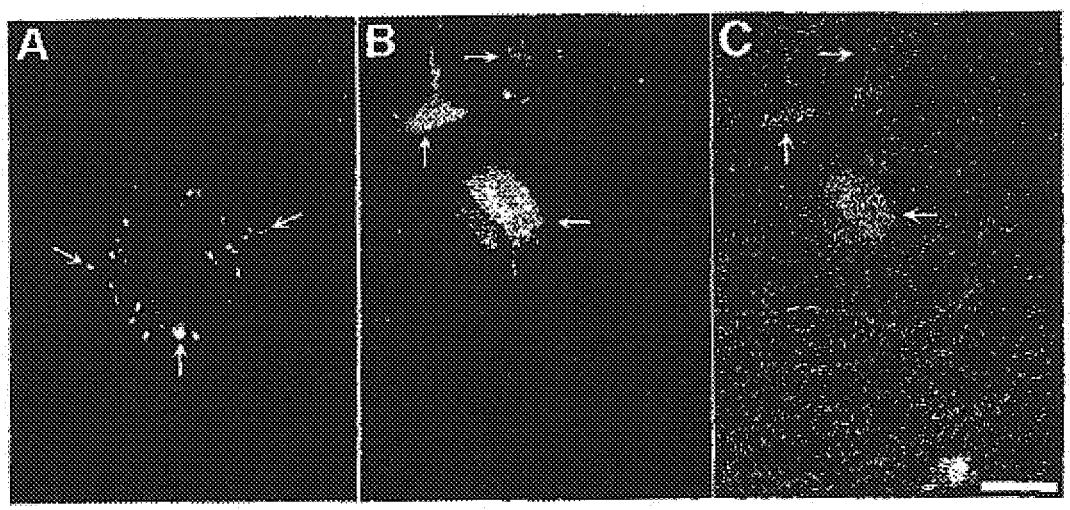
FIG. 19 describes expression of GFP in plated allantoic explants at low magnification (FIG. 19A) fluorescence view, higher magnification (FIG. 19B) of GFP-expressing mesenchymal cells from FIG. 19A, and simultaneous bright field/fluorescent view (FIG. 19C) of those GFP-expressing mesenchymal cells from FIG. 19B.

Transfected cells were scored (Table 6). The only cells that took up and expressed GFP in both the 12- and 18-hour cultures were the peripheral fibroblast-like cells that were adherent to the bottom of the dish (FIG. 19). FIG. 19 describes expression of GFP in plated allantoic explants. (FIG. 19A): Low magnification fluorescence view of GFP-expressing adherent mesenchymal cells in an allantoic explant that had been cultured for 12 hours prior to transfection. Expressing cells are green (white arrows) and are localized to the periphery of the explant. (FIG. 19B): Higher magnification of GFP-expressing mesenchymal cells (white arrows) from (19A). (FIG. 19C): Simultaneous bright field/fluorescent view of those GFP-expressing mesenchymal cells from (FIG. 19B) (white arrows) to show that they are distinctly different from cells contained within endothelial cell channels (black arrow). Scale bar in (FIG. 19C): 500 μm (FIG. 19A); 50 μm (FIGS. 19B, C).

In the younger cultures, most of these cells were located at the explant periphery (FIG. 19) but, in older cultures, many adherent cells beneath the vasculature were also positive (data not shown). Plated allantoises exposed to the precipitate at both 12- and 18-hours after explantation took up DNA with similar frequencies (5.5% versus 6.0%, respectively, Table 6). The vasculature and overlying mesothelial cells contained no detectable GFP, suggesting that allantoic angioblasts (pre-endothelial cells), endothelial and mesothelial cells are either refractory to uptake of DNA by this standard method of transfection or, if they can take it up, are unable to express it. In addition, fewer cells were found on average in transfected cultures as compared with the controls (Table 6), suggesting that some allantoic cells may be sensitive to calcium phosphate.

because mesothelium is thought to provide signals required for vascularization of core mesoderm (K. M. Downs, et al., supra, 1998). Mesenchymal cells were classified on the basis of several criteria: (i) they were present as spindle-shaped adherent cells at the periphery of the explants, (ii) they did not express flk-1 or VCAM1, (iii) they survived and proliferated in low serum, and (iv) some of them took up, incorporated and expressed GFP via calcium phosphate precipitation. The presence of mesenchyme beneath the necrotic vasculature in low serum also suggested that these cells underlie the explants throughout the entire culture period. Thus, we have established that the gross topographical relationships between cell populations in allantoic explants from top to bottom are: mesothelium, endothelium, and mesenchyme.

In addition to the foregoing results, appropriate integration of cultured allantoic cells into host allantoises following transplantation suggested that normal allantoic phenotype is maintained in culture. The majority of colonizing donor cells were endothelial and some also expressed flk-1; the fewest were mesothelial, and the others were mesenchymal, neither part of the vasculature nor the mesothelium. Because cultured allantoic cells retained lacZ activity for up to 72 hours,

| No. | Number Cells/Allantois Early Vascularization (number of allantoises) | | | | Number Cells/Allantois Post Vascularization (number of allantoises) | | | |
|---|---|---|---|---|---|---|---|---|
| | Control | FCS | Transfected | % Transfection Efficiency | Control | FCS | Transfected | % Transfection Efficiency |
| 1 | 7933 (3) | 6240 (3) | 2375 (8) | 7.3 | 2760 (3) | 3083 (3) | 3850 (10) | 3.4 |
| 2 | 5375 (2) | 2313 (2) | 1358 (2) | 7.7 | 3910 (2) | 4252 (2) | 2814 (8) | 11.3 |
| 3 | 6210 (3) | 4550 (3) | 5145 (3) | 1.4 | 6460 (3) | 7700 (3) | 3635 (9) | 3.4 |
| Average | 6506 (8) | 4368 (8) | 2959 (13) | 5.5 | 4377 (8) | 5012 (8) | 3433 (27) | 6.0 |

Table 6. transfection efficiency of headfold-stage allentoises cultured for 12 and 18 hours. Headfold-stage allantoises were explanted onto 24-well tissue culture plates and cultured for 12 and 18 hours, at which time they were transfected for 6 hours with a plasmid containing GFP. The percent transfection efficiency was calculated as the total number of GFP-expressing cells over the total number of allantoic cells per treatment group.

Discussion

Characterization of Allantoic Explants

In the Examples above, we have demonstrated that explanted murine allantoises cultured in a high concentration of rat serum rapidly and reproducibly undergo vasculogenesis. Morphological vascularization was evident as early as 12 hours after plating onto tissue culture plastic. With feeding, most allantoises proliferated and maintained a Flk-1-positive vasculature for at least 72 hours.

Cultured allantoises contained four identifiable cell types, angioblasts, endothelial, mesothelial and mesenchymal cells, all of which were normally present in intact allantoises of whole conceptuses. Use of antibodies to illuminate the nature of these cells was validated by determining the location of Flk-1 and VCAM-1 in intact allantoises of both freshly-recovered and cultured conceptuses. We found that angioblasts were present as unvascularized Flk-1 cells in explants cultured in low serum; VEGF promoted their survival and morphogenesis into vessels. Endothelial cells were present in both plated and suspended allantoises as Flk-1-containing vascular channels. Mesothelium was identified by expression of VCAM1 in cells that overlay the vasculature; its presence in the cultures is significant and allantoises have previously been shown to maintain lacZ expression at all developmental stages examined (K. M. Downs and C. Harmann, supra, 1995; K. M. Downs, et al., supra, 1998), loss of approximately one-third of injected cells during transplantation was likely due to leakage from the site of injection as cells were blown into the allantois rather than to loss of lacZ expression. Loss of another third of injected cells by clumping at the site of integration into the host was likely due to sub-optimal trypsinization (10 minutes rather than 20 minutes) in an effort to ensure cell viability rather than loss due to spurious differentiation because disruption of the stereotypic organization of the allantoic cultures was never observed. Alternatively, 8 hours may have been inadequate to ensure integration and maximal donor cell dispersal following transplantation. Culture periods beyond 36 hours were not used because global tissue necrosis had previously been observed despite feeding and culture of conceptuses individually (S. Gifford and K. M. Downs, unpublished observations).

Although initially favorable to vasculogenesis, conditions that employed 8-well chamber slides did not maintain vascularization in the explants despite feeding. This observation was not further explored, but one explanation may be that the optimal surface area: volume ratio of medium in these culture vessels had not been achieved. Although vasculogenesis took place in 5% FCS, the ensuing vasculature was neither extensive nor retained beyond 24 hours. Increasing concentrations of serum were only a partial solution, and did not enable adequate maintenance of the vasculature for 72 hours. We conclude from this that a high concentration of some serum factor(s) must be required for both formation and maintenance of endothelial cells in allantoic explants. The identification of that factor and its normal site of production in the conceptus are not, however, known.

The Role of VCAM1 in Differentiation and Function of The Murine Allantois

VCAM-1, originally isolated as a cytokine-inducible adhesion molecule in human umbilical vein endothelial cells (L. C. Osborn, et al., Cell 59:1203–1211, 1989; M. Elices, et al., Cell 60:577–584, 1990; reviewed in L. Kwee, et al., supra, 1995) is required, along with its counter-receptor, $\alpha 4$ integrin, for chorioallantoic fusion (G. C. Gurtner, et al., supra, 1995; L. Kwee, et al., supra, 1995; J. T. Yang, et al., supra, 1995). $\alpha 4$ integrin is expressed in the chorion, and VCAM1 in the distal allantois, though the expressing cell types were not identified (J. T. Yang, et al., supra, 1995; L. Kwee, et al., supra, 1995; G. C. Gurtner, et al., supra, 1995). Following chorioallantoic attachment, the allantoic vasculature spreads onto the chorion and penetrates the chorionic disk and labyrinth (K. Theiler, *The House Mouse*, 1989). The role, if any, of VCAM-1 and $\alpha 4$-integrin in events other than attachment is, however, far from clear.

VCAM-1 was first detectable in a few distal mesothelial cells at the headfold stage, but not earlier. Expression of VCAM1 in mesothelium was then observed in all allantoic stages thereafter, spreading proximally and increasing over time. Elevated levels of VCAM-1 agree with our previous prediction that the rate of chorioallantoic fusion would be dependent upon increasing levels of a required adhesion factor during allantoic maturation in the exocoelom (K. M. Downs and R. L. Gardner, supra, 1995; K. M. Downs, supra, 1998). In the allantoic core, VCAM-1-containing cells were intimately associated with but distinct from Flk-1-positive endothelium. A role for these cells in endothelial support is unlikely, as they were not found associated with the Flk-1 vasculature in the basal region. One intriguing possibility is that the VCAM-1-containing core cells mediate vascularization of the chononic and labyrinthine layers via VCAM-1 interactions, pulling the vasculature along as chorioallantoic adhesion proceeds.

Finally, our observation that expression of VCAM1 begins in the distal most region of the allantois at the headfold stage supports previous tests of developmental potency in headfold-stage allantoises (K. M. Downs and C. Harmann, supra, 1997). When placed into the primitive streak of host fetuses at the level of emerging lateral plate mesoderm, distal donor allantoic cells were often extruded from rather than integrated into the host. In light of the spatiotemporal expression patterns of VCAM1, poor colonization was likely due to cell surface incompatibilities related to VCAM1, which is not expressed in the posterior region of the fetus (G. C. Gurtner, et al., supra, 1995; L. Kwee, et al., supra, 1995; this study, data not shown). The few distal donor allantoic cells that integrated into host blood vessels likely did so as a result of their Flk-1 status and, therefore, endothelial nature.

Taken together, our results provide strong evidence that allantoic explants are a new and practical system for the study of vasculogenesis. Given the apparent lability of the vascular plexus to undergo rearrangement over 72-hours in culture, allantoises cultured in vitro may also shed light on the process of vascular remodeling. Lastly, the ability of allantoic cells to be genetically-manipulated and to colonize the developing allantois may prove therapeutically valuable for in utero gene therapy in cases where a blood-borne circulating factor might ameliorate or cure certain fetal defects.

I claim:

1. A method of determining whether a compound alters the development of allantoic mesoderm into blood vessels in vitro comprising:

a) isolating a first and second allantoic tissue;

b) culturing the first and second allantoic tissues in vitro;

c) treating the first allantoic tissue with a compound, but not treating the second allantoic tissue with said compound; and d) observing the development of allantoic mesoderm into blood vessels in the first and second allantoic tissues, wherein an alteration in the development of allantoic mesoderm into blood vessels in the first allantoic tissue as compared to the second allantoic tissue indicates the compound alters the development of allantoic mesoderm into blood vessels.

2. The method of claim 1 wherein the test compound is a protein.

* * * * *